(12) United States Patent
Iwano et al.

(10) Patent No.: US 10,874,837 B2
(45) Date of Patent: Dec. 29, 2020

(54) BALLOON CATHETER

(71) Applicant: GOODMAN CO., LTD., Nagoya (JP)

(72) Inventors: Kenshi Iwano, Seto (JP); Takamasa Miyake, Seto (JP); Takafumi Mizuno, Seto (JP); Tomokazu Ogawa, Seto (JP); Keisuke Ogawa, Seto (JP); Soichiro Fujisawa, Seto (JP); Mitsuhiro Ota, Seto (JP); Yuki Nakagawa, Seto (JP)

(73) Assignee: GOODMAN CO., LTD., Nagoya (JP)

(*) Notice: Subject to any disclaimer, the term of this patent is extended or adjusted under 35 U.S.C. 154(b) by 309 days.

(21) Appl. No.: 15/727,665

(22) Filed: Oct. 9, 2017

(65) Prior Publication Data

US 2018/0043140 A1 Feb. 15, 2018

Related U.S. Application Data

(63) Continuation-in-part of application No. PCT/JP2016/061484, filed on Apr. 8, 2016.

(30) Foreign Application Priority Data

Apr. 10, 2015 (JP) ................. 2015-080627
Dec. 21, 2015 (JP) ................. 2015-248540

(51) Int. Cl.
*A61M 25/10* (2013.01)
*A61B 17/3207* (2006.01)
*A61B 17/22* (2006.01)

(52) U.S. Cl.
CPC ... *A61M 25/104* (2013.01); *A61B 17/320725* (2013.01); *A61M 25/1006* (2013.01);
(Continued)

(58) Field of Classification Search
CPC ............ A61M 25/104; A61M 25/1006; A61M 25/1002; A61M 25/1038;
(Continued)

(56) References Cited

U.S. PATENT DOCUMENTS 5,196,024 A 3/1993 Barath
5,797,935 A * 8/1998 Barath ............. A61B 17/32072
606/159

(Continued)

FOREIGN PATENT DOCUMENTS

CN 101420913 A 4/2009
EP 565796 A1 10/1993
(Continued)

OTHER PUBLICATIONS

JP 2012096121A Dated: Jan. 2012; English Machine Translation (Oct. 18, 2019).*
(Continued)

*Primary Examiner* — Katrina M Stransky
(74) *Attorney, Agent, or Firm* — Banner & Witcoff, Ltd.

(57) ABSTRACT

A balloon catheter includes a balloon/shaft assembly and a linear member. The balloon/shaft assembly includes a catheter shaft extending from a proximal end to a distal end and a balloon connected to the catheter shaft. The linear member straddles an inflatable region of the balloon and is mounted on the balloon/shaft assembly. The linear member includes a hard portion and a flexible portion. The hard portion includes at least an outer portion disposed on an opposite side to an inner portion facing the inflatable region, of a portion disposed along an outer peripheral surface of the inflatable region in an inflated state. The flexible portion is a portion other than the hard portion. The flexible portion is extendable and has a lower hardness than the hard portion.

28 Claims, 22 Drawing Sheets

(52) U.S. Cl.
CPC .............. *A61B 2017/22061* (2013.01); *A61M 25/1002* (2013.01); *A61M 25/1038* (2013.01); *A61M 2025/107* (2013.01); *A61M 2025/109* (2013.01); *A61M 2025/1079* (2013.01); *A61M 2025/1086* (2013.01)

(58) Field of Classification Search
CPC .... A61M 2025/107; A61M 2025/1079; A61M 2025/1086; A61M 2025/109; A61B 17/320725; A61B 17/32075; A61B 2017/22061
See application file for complete search history.

(56) References Cited

U.S. PATENT DOCUMENTS

| | | |
|---|---|---|
| 7,993,358 B2 | 8/2011 | O'Brien |
| 8,454,637 B2 | 6/2013 | Aggerholm et al. |
| 2003/0153870 A1 | 8/2003 | Meyer et al. |
| 2003/0229370 A1 | 12/2003 | Miller |
| 2004/0034384 A1 | 2/2004 | Fukaya |
| 2006/0106412 A1 | 5/2006 | Crow et al. |
| 2006/0111736 A1 | 5/2006 | Kelley |
| 2006/0184191 A1 | 8/2006 | O'Brien |
| 2007/0213761 A1 | 9/2007 | Murphy et al. |
| 2009/0192537 A1 | 7/2009 | O'Brien |
| 2012/0130407 A1 | 5/2012 | Aggerholm et al. |
| 2012/0191111 A1* | 7/2012 | Aggerholm .... A61B 17/320725 606/159 |

FOREIGN PATENT DOCUMENTS

| | | |
|---|---|---|
| JP | 2005-517474 A | 6/2005 |
| JP | 2008-00276 A | 1/2008 |
| JP | 2008-067994 A | 3/2008 |
| JP | 2008-529658 A | 8/2008 |
| JP | 2009-112361 A | 5/2009 |
| JP | 2011098060 A | 5/2011 |
| JP | 2011-245114 A | 12/2011 |
| JP | 2012-096121 A | 5/2012 |
| JP | 2014-506140 A | 3/2014 |
| WO | 2003-013642 A1 | 2/2003 |
| WO | 2012-029109 A1 | 3/2012 |
| WO | 2012-099950 A1 | 7/2012 |
| WO | 2016-163495 A1 | 10/2016 |

OTHER PUBLICATIONS

Jun. 14, 2016—International Search Report—Intl App PCT/JP2016/061484.
Oct. 11, 2018—(EP) Extended Search Report—App 16776661.7.
Apr. 15, 2019—(EP) Office Action—App 16776661.7.
Oct. 10, 2017—(WO) IPRP and Written Opinion—App PCT/JP2016/061484, Eng Tran.
Oct. 29, 2019—(JP) Notification of Reasons for Rejection—App 2017-511077, Eng Tran.
Nov. 4, 2019—(CN) First Office Action—App 201680013072.7, Eng Tran.
Apr. 28, 2020—(JP) Decision of Rejection—App 2017-511077, Eng Tran.
May 15, 2020—(CN) The Second Office Action—App 201680013072.7, Eng Tran.
Oct. 19, 2020—(CN) Rejection Decision—App 201680013072.7, Eng Tran.

* cited by examiner

PROXIMAL END ←          → DISTAL END

PROXIMAL END ←          → DISTAL END

PROXIMAL END ← → DISTAL END

PROXIMAL END ⟵　　　　　　　　　　⟶ DISTAL END

PROXIMAL END ← → DISTAL END

PROXIMAL END ⬅——— ———➤ DISTAL END

PROXIMAL END ⬅            ➡ DISTAL END

PROXIMAL END ← → DISTAL END

PROXIMAL END ⟵          ⟶ DISTAL END

BALLOON CATHETER

CROSS-REFERENCE TO RELATED APPLICATION

This application is a continuation-in-part of International Application No. PCT/JP2016/061484, filed Apr. 8, 2016, which claims priority from Japanese Patent Applications No. 2015-080627, filed on Apr. 10, 2015 and No. 2015-248540, filed on Dec. 21, 2015. The disclosure of the foregoing applications is hereby incorporated by reference in its entirety.

BACKGROUND

The present disclosure relates to a balloon catheter.

A balloon catheter is known that is used in treatments that dilate a constricted location of a blood vessel. For example, the known balloon catheter is provided with a catheter tube, a balloon, three linear members, and a fixed cone-shaped portion. The catheter tube (sometimes also referred to as a "catheter shaft") has an inner tube and an outer tube. The balloon is joined to the outer tube and the inner tube. The balloon inflates when a compressed fluid is supplied. The three linear members are disposed on the outer peripheral side of the balloon. A distal end side of the fixed cone-shaped portion is joined to a distal end of the inner tube. A proximal end side of the fixed cone-shaped portion is joined to the three linear members. The fixed cone-shaped portion is elastically deformable. The three linear members move in a direction away from the inner tube in accordance with the inflation of the balloon. The fixed cone-shaped portion extends in response to the movement of the three linear members in the direction away from the inner tube. The fixed cone-shaped portion contracts in accordance with the deflation of the balloon, and the three linear members move in a direction approaching the inner tube.

SUMMARY

In the case of the known balloon catheter, the fixed cone-shaped portion joined to the distal end of the inner tube has an outer diameter that is sufficiently larger than the inner tube even in a deflated state. Thus, from the point of view of crossability, there is room for improvement.

Various embodiments of the broad principles derived herein provide a balloon catheter having superior crossability.

Embodiments provide a balloon catheter that includes a balloon/shaft assembly and a linear member. The balloon/shaft assembly includes a catheter shaft extending from a proximal end to a distal end and a balloon connected to the catheter shaft. The balloon has an inflatable region configured to inflate outward in a radial direction around the catheter shaft. The linear member straddles the inflatable region of the balloon and is mounted on the balloon/shaft assembly at a distal end position located further toward the distal end side than the inflatable region and at a proximal end position located further toward the proximal end side than the inflatable region. The linear member includes a hard portion and a flexible portion. The hard portion includes at least one outer portion disposed on an opposite side to an inner portion facing the inflatable region, of a portion disposed along an outer peripheral surface of the inflatable region in an inflated state. The flexible portion is a portion other than the hard portion. The flexible portion is extendable and has a lower hardness than the hard portion.

BRIEF DESCRIPTION OF THE DRAWINGS

Embodiments will be described below in detail with reference to the accompanying drawings in which.

DETAILED DESCRIPTION

First Embodiment

Figure 1:
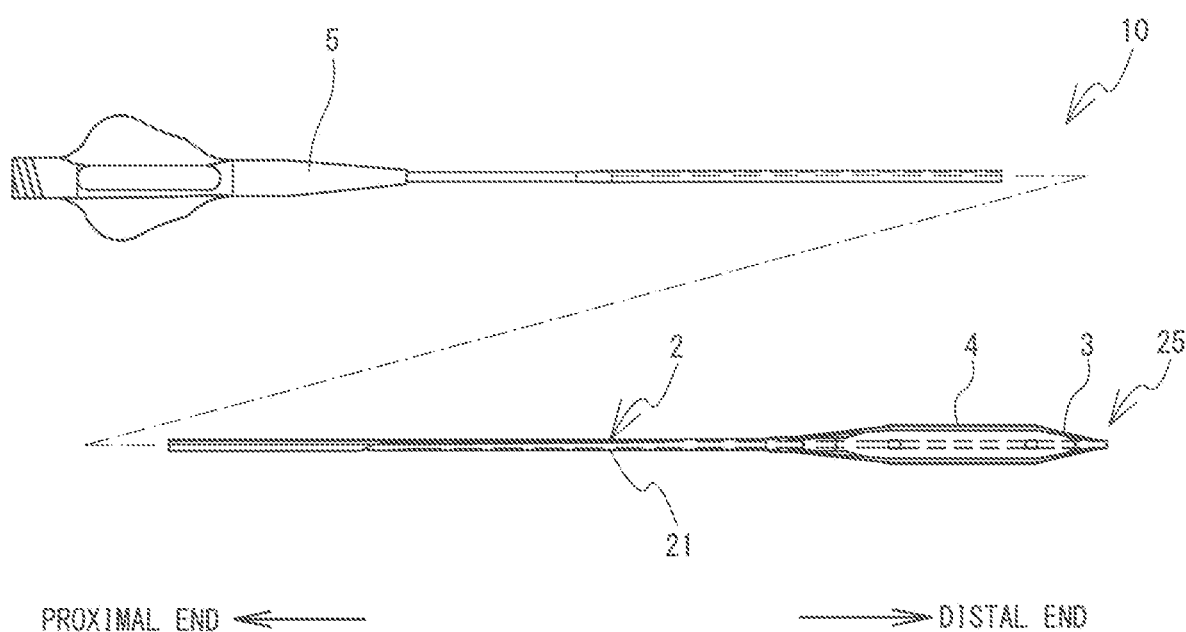
FIG. 1 is a side view of a balloon catheter according to a first embodiment.

Hereinafter, a balloon catheter 10 according to a first embodiment of the present disclosure will be explained with reference to FIG. 1 to FIG. 8. As shown in FIG. 1, the balloon catheter 10 has a catheter shaft 2, a balloon 3, and linear members 4A, 4B, and 4 C (refer to FIG. 3, hereinafter collectively referred to as "linear members 4"). Hereinafter, the catheter shaft 2 and the balloon 3 are collectively referred to as a "balloon/shaft assembly 25." The balloon 3 is connected to an end portion on one side of the catheter shaft 2. The linear members 4 are disposed on the outside of the balloon 3 in an inflated state. The balloon catheter 10 is used in a state in which a hub 5 is connected to an end portion on the other side of the catheter shaft 2. The hub 5 can supply compressed fluid to the balloon 3 via the catheter shaft 2. Hereinafter, the one end (of both ends) of the catheter shaft 2 on the one side is referred to as a "distal end." The other end (of both ends) of the catheter shaft 2 is referred to as a "proximal end." A direction extending along the catheter shaft 2 is referred to as an "extending direction." In a plane orthogonal to the extending direction, of a radial direction taking a center of a cross section of the catheter shaft 2 as a reference, a side closer to the center of the cross section of the catheter shaft 2 is referred to as an "inner side" and a side further away from the center of the cross section of the catheter shaft 2 is referred to as an "outer side."

Catheter Shaft 2

Figure 4:
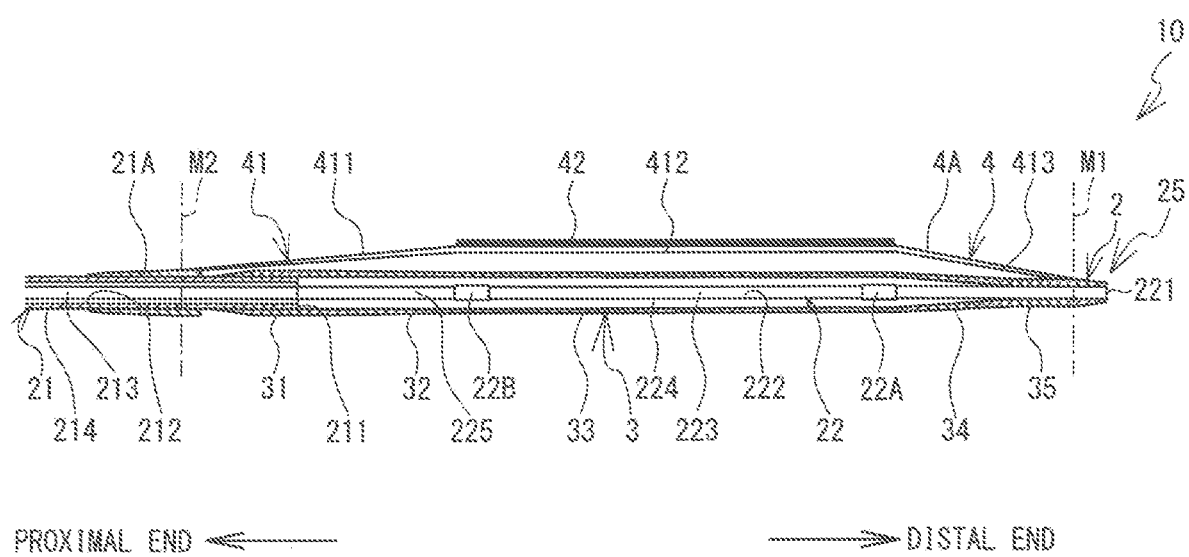
FIG. 4 is a cross-sectional view of the balloon and the linear member in the deflated state.
Figure 7:
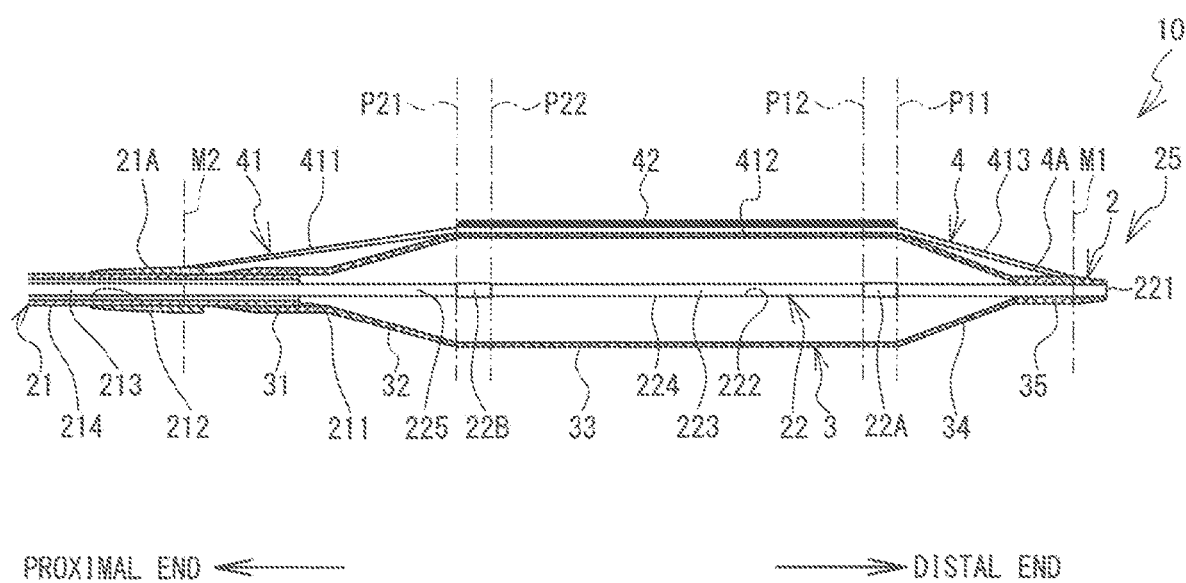
FIG. 7 is a cross-sectional view of the balloon and the linear member in the inflated state.

As shown in FIG. 4 and FIG. 7, the catheter shaft 2 has an outer tube 21 and an inner tube 22. The outer tube 21 and the inner tube 22 are both flexible tubular members. The outer tube 21 has a lumen 213, which is a space surrounded by an inner surface 212, which is a surface on the inner side of the outer tube 21. The inner tube 22 has a lumen 223, which is a space surrounded by an inner surface 222, which is a surface on the inner side of the inner tube 22. The outer tube 21 and the inner tube 22 are formed of a polyamide resin. The inner diameter of the outer tube 21 is larger than the outer diameter of the inner tube 22.

Apart from a predetermined portion on the distal end side, the inner tube 22 is disposed inside the lumen 213 of the outer tube 21. The predetermined portion on the distal end side of the inner tube 22 protrudes toward the distal end side from an end (hereinafter referred to as a "distal end 211") on the distal end side of the outer tube 21. The end (hereinafter referred to as a "distal end 221") on the distal end side of the inner tube 22 is disposed further toward the distal end side than the distal end 211 of the outer tube 21. Hereinafter, the predetermined portion on the distal end side of the inner tube 22 is referred to as a "protruding portion 225." Radiopaque markers (hereinafter simply referred to as "markers") 22A and 22B are fitted to the protruding portion 225 of the inner tube 22. Resin into which a radiopaque material is mixed is used as the material of the markers 22A and 22B. The markers 22A and 22B are fixed to an outer surface 224, which is an outer peripheral surface of the inner tube 22, as a result of cylindrical members formed of the above-described material being crimped onto the protruding portion 225 of the inner tube 22. The markers 22A and 22B have a predetermined length in the extending direction. The markers 22A and 22B do not allow the passage of radiation. The marker 22A is disposed further toward the distal end side than the marker 22B. The markers 22A and 22B are separated from each other in the extending direction.

As shown in FIG. 2, FIG. 4, FIG. 5, and FIG. 7, of an outer surface 214, which is the outer peripheral surface of the outer tube 21, a mounting member 21A is mounted on a portion further toward the proximal end side than the distal end 211. The mounting member 21A is a cylindrical member that can move along the extending direction. The inner diameter of the mounting member 21A is larger than the outer diameter of the outer tube 21. A thermoplastic resin, such as a polyamide resin or the like, is used as the material of the mounting member 21A.

As shown in FIG. 4 and FIG. 7, the compressed fluid supplied from the hub 5 (refer to FIG. 1) flows through a space of the lumen 213 of the outer tube 21 other than the lumen 223 of the inner tube 22. The balloon 3 inflates (refer to FIG. 5 to FIG. 7) in accordance with the supply of the compressed fluid. A guide wire that is not shown in the drawings is inserted through the lumen 223 of the inner tube 22

The material of the outer tube 21 and the inner tube 22 is not limited to the polyamide resin, and can be changed to another flexible material. For example, a synthetic resin material, such as a polyethylene resin, a polypropylene resin, a polyurethane resin, a polyimide resin and the like, may be used as the material of the outer tube 21 and the inner tube 22. Additives may be mixed with the synthetic resin material. Different synthetic resin materials may be used as the materials of the outer tube 21 and the inner tube 22, respectively. The material of the markers 22A and 22B is not limited to the resin into which the radiopaque material is mixed, and can be changed to another material that does not allow the passage of radiation. For example, a resin on which a radiopaque material is deposited, or a material such as metal or the like that does not allow the passage of radiation may be used as the material of the markers 22A and 22B.

Balloon 3

Figure 2:
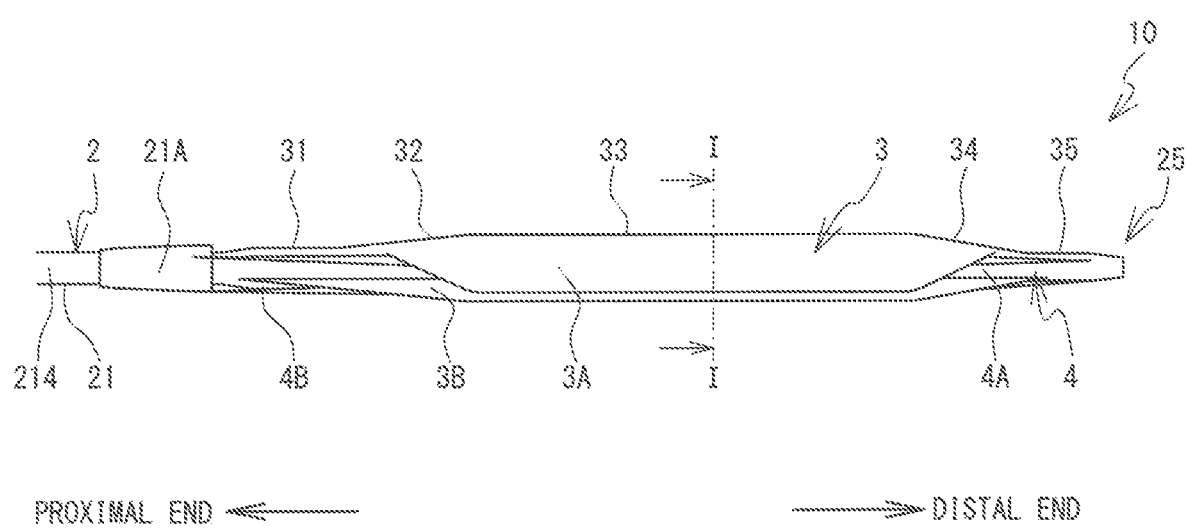
FIG. 2 is a side view of a balloon and a linear member in a deflated state.
Figure 3:
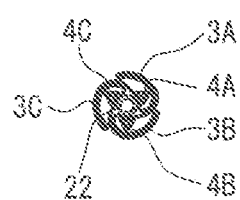
FIG. 3 is a cross-sectional view in the direction of arrows along a line I-I shown in FIG. 2.
Figure 5:
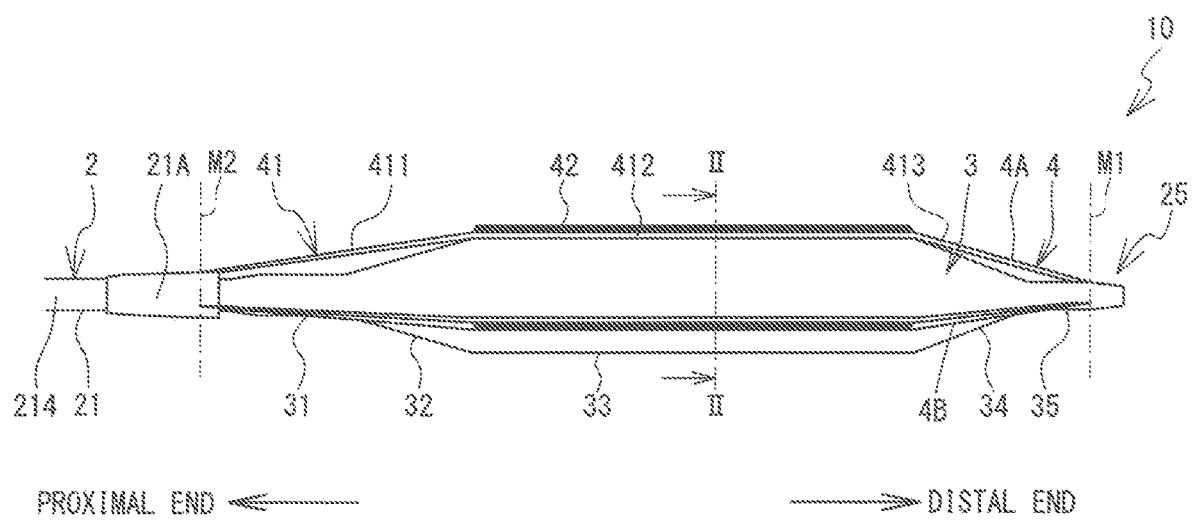
FIG. 5 is a side view of the balloon and the linear member in an inflated state.
Figure 6:
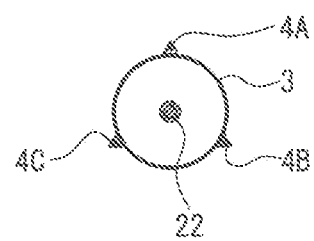
FIG. 6 is a cross-sectional view in the direction of arrows along a line II-II shown in FIG. 5.

As shown in FIG. 2 to FIG. 4, the balloon 3 deflates to the inner side when the compressed fluid is not supplied. As shown in FIG. 5 to FIG. 7, the balloon 3 inflates to the outer side when the compressed fluid is supplied. The balloon 3 is formed of a polyamide resin. As shown in FIG. 2, FIG. 4, FIG. 5, and FIG. 7, the balloon 3 includes a proximal end side leg portion 31, a proximal end side cone region 32, an inflatable region 33, a distal end side cone region 34, and a distal end side leg portion 35. The proximal end side leg portion 31, the proximal end side cone region 32, the inflatable region 33, the distal end side cone region 34, and the distal end side leg portion 35 respectively correspond to portions of the balloon 3 divided into five in the extending direction. The length of the inflatable region 33 in the extending direction is longer than the respective lengths in the extending direction of the proximal end side leg portion 31, the proximal end side cone region 32, the distal end side cone region 34, and the distal end side leg portion 35.

As shown in FIG. 4 and FIG. 7, the proximal end side leg portion 31 is connected, by thermal welding, to the outer surface 214 that is the outer peripheral surface of the outer tube 21, at a portion located further toward the proximal end side than the distal end 211 and further toward the distal end side than the portion on which the mounting member 21A is mounted. The proximal end side cone region 32 is adjacent to the distal end side of the proximal end side leg portion 31. The inflatable region 33 is adjacent to the distal end side of the proximal end side cone region 32. The distal end side cone region 34 is adjacent to the distal end side of the inflatable region 33. The distal end side leg portion 35 is adjacent to the distal end side of the distal end side cone region 34. The distal end side leg portion 35 is connected, by thermal welding, to the outer surface 224 of the protruding portion 225 of the inner tube 22, at a portion located further toward the proximal end side than the distal end 221. The proximal end side leg portion 31, the proximal end side cone region 32, the inflatable region 33, the distal end side cone region 34, and the distal end side leg portion 35 are disposed side by side in that order from the proximal end side toward the distal end side. The proximal end side cone region 32, the inflatable region 33, the distal end side cone region 34, and the distal end side leg portion 35 cover the protruding portion 225 of the inner tube 22 from outside.

As shown in FIG. 2 to FIG. 4, three pleats are formed by the balloon 3 in the deflated state. The balloon 3 is a three pleat type balloon. As shown in FIG. 3, in the deflated state, the balloon 3 is folded over so as to form three pleats 3A, 3B, and 3C. Each of the pleats 3A, 3B, and 3C is wrapped around the protruding portion 225 of the inner tube 22. In this state, the pleat 3A covers the linear member 4A, which will be described later, from outside. The pleat 3B covers the linear member 4B, which will be described later, from outside. The pleat 3C covers the linear member 4C, which will be described later, from outside. The pleats 3A, 3B, and 3C are also called "flaps" and "wings."

The inflated state of the balloon 3 will be explained with reference to FIG. 5 to FIG. 7. As shown in FIG. 6, the cross-sectional shape of the balloon 3 is circular. As shown in FIG. 5 and FIG. 7, the proximal end side cone region 32 has a tapered shape. The diameter of the proximal end side cone region 32 increases continuously and linearly from the proximal end side toward the distal end side. The diameter of the inflatable region 33 is the same across the whole length in the extending direction. The distal end side cone region 34 has a tapered shape. The diameter of the distal end side cone region 34 decreases continuously and linearly from the proximal end side toward the distal end side. The diameter of the cross section of the balloon 3 changes in a stepped manner between the proximal end side cone region 32, the inflatable region 33, and the distal end side cone region 34. The inflatable region 33 is a portion of the balloon 3 having the maximum diameter.

As shown in FIG. 7, a boundary of the inflatable region 33 on the distal end side is aligned, in the extending direction, with a position P11 of an end portion on the distal end side of the marker 22A. In other words, the boundary of the inflatable region 33 on the distal end side is a position of a boundary between the inflatable region 33 and the distal end side cone region 34. A boundary of the inflatable region 33 on the proximal end side is aligned, in the extending direction, with a position P21 of an end portion on the proximal end side of the marker 22B. In other words, the boundary of the inflatable region 33 on the proximal end side is a position of a boundary between the inflatable region 33 and the proximal end side cone region 32.

The material of the balloon 3 is not limited to the polyamide resin, and can be changed to another flexible material. For example, a polyethylene resin, a polypropylene resin, a polyurethane resin, a polyimide resin, silicone rubber, natural rubber, and the like may be used as the material of the balloon 3. In the above description, the method of connecting the outer tube 21 and the inner tube 22 to the balloon 3 is not limited to the thermal welding. For example, each of the outer tube 21 and the inner tube 22 may be connected using an adhesive.

Linear Member 4

The linear member 4 will be explained with reference to FIG. 4 to FIG. 8. The linear member 4 has a restoring force with respect to bending deformation. The linear member 4 is a monofilament-shaped elastic body. The linear members 4A, 4B, and 4C have the same shape. The linear member 4 extends along the extending direction.

As shown in FIG. 4, FIG. 5, and FIG. 7, an end portion on the distal end side of the linear member 4 is connected, by thermal welding, to a portion of the outer peripheral surface of the distal end side leg portion 35 of the balloon 3 that is further to the distal end side than the center in the extending direction. Hereinafter, a position at which the end portion on the distal end side of the linear member 4 is connected, in the extending direction of the balloon catheter 10, is referred to as a "distal end position M1." In the extending direction, the distal end position M1 is disposed further toward the distal end side than the inflatable region 33 of the balloon 3 in the inflated state. The distal end position M1 corresponds to a position further toward the distal end side than the center, in the extending direction, of the distal end side leg portion 35 of the balloon 3. The end portions on the distal end side of each of the linear members 4A, 4B, and 4C are connected, respectively, to positions that divide the outer peripheral surface of the distal end side leg portion 35 of the balloon 3 into three equal parts in the circumferential direction.

An end portion on the proximal end side of the linear member 4 is connected, by thermal welding, to a portion of the outer peripheral surface of the mounting member 21A located further toward the proximal end side than the center in the extending direction. Hereinafter, a position at which the end portion on the proximal end side of the linear member 4 is connected, in the extending direction of the balloon catheter 10, is referred to as a "proximal end position M2." In the extending direction, the proximal end position M2 is disposed further toward the proximal end side than the inflatable region 33 of the balloon 3 in the inflated state. The end portions on the proximal end side of each of the linear members 4A, 4B, and 4C are connected, respectively, to positions that divide the outer peripheral surface of the mounting member 21A into three equal parts in the circumferential direction. The linear member 4 is connected at the distal end position M1 and the proximal end position M2, and is not connected to the balloon 3 at other portions thereof.

The linear member 4 is disposed between the distal end position M1 and the proximal end position M2 so as to straddle the inflatable region 33 of the balloon 3. As shown in FIG. 6, when the balloon 3 is in the inflated state, the linear members 4A, 4B, and 4C extend in straight lines in the extending direction, respectively, at positions that divide the outer peripheral surface of the inflatable region 33 of the balloon 3 into three approximately equal parts in the circumferential direction.

As shown in FIG. 4, FIG. 5, and FIG. 7, the linear member 4 has a flexible portion 41, and a hard portion 42. The flexible portion 41 extends between the proximal end position M2 and the distal end position M1. The flexible portion 41 includes a first portion 411, a second portion 412, and a third portion 413. The first portion 411, the second portion 412, and the third portion 413 respectively correspond to portions of the flexible portion 41 that is divided into three in the extending direction. An end portion on the proximal end side of the first portion 411 is connected to the outer peripheral surface of the mounting member 21A, at the proximal end position M2. The second portion 412 is adjacent to the distal end side of the first portion 411. The third portion 413 is adjacent to the distal end side of the second portion 412. An end portion on the distal end side of the third portion 413 is connected to the outer peripheral surface of the distal end side leg portion 35 of the balloon 3, at the distal end position M1. The hard portion 42 is laminated on the second portion 412 of the flexible portion 41, at a portion on the opposite side to a portion facing the balloon 3.

Figure 8:
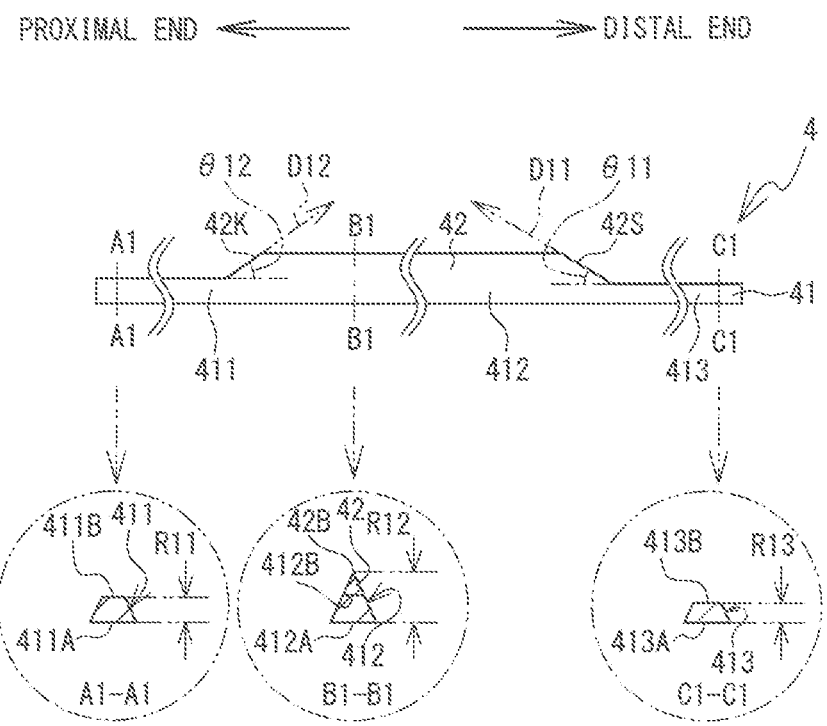
FIG. 8 shows a side view and cross-sectional views of the linear member 4.

FIG. 8 shows cross sections of the linear member 4 at each of a line A1-A1, a line B1-B1, and a line C1-C1. The cross-sectional shape of the linear member 4 is a trapezoid shape or a triangular shape. This is explained more specifically below.

The cross-sectional shape of the flexible portion 41 (the first portion 411 to the third portion 413) is a trapezoid shape. Hereinafter, of the first portion 411 of the flexible portion 41, a portion facing the balloon 3 in the inflated state (refer to FIG. 6) is referred to as an "inner portion 411A." Of the first portion 411, a portion on the opposite side to the inner portion 411A is referred to as an "outer portion 411B." Of the second portion 412 of the flexible portion 41, a portion facing the balloon 3 in the inflated state is referred to as an "inner portion 412A." Of the first portion 412, a portion on the opposite side to the inner portion 412A is referred to as an "outer portion 412B." Of the third portion 413 of the flexible portion 41, a portion facing the balloon 3 is referred to as an "inner portion 413A." Of the third portion 413, a portion on the opposite side to the inner portion 413A is referred to as an "outer portion 413B." The inner portions 411A, 412A, and 413A and the outer portions 411B, 412B, and 413B respectively correspond to a lower base and an upper base of the trapezoid that is the cross-sectional shape.

A length between the inner portion 413A and the outer portion 413B of the third portion 413, namely, a thickness R13 of a portion of the flexible portion 41 located further toward the distal end side than the hard portion 42, is 0.15 mm. A length between the inner portion 411A and the outer portion 411B of the first portion 411, namely, a thickness R11 of a portion of the flexible portion 41 located further toward the proximal end side than the hard portion 42, is 0.23 mm. The thickness R13 is narrower than the thickness R11.

The shape of the cross section of the hard portion 42 is an equilateral triangle shape having the outer portion 412B of the second portion 412 as one side. The hard portion 42 protrudes to the outside from the outer portion 412B of the second portion 412 of the flexible portion 41. Hereinafter, an end portion on the outside of the hard portion 42 is referred to as an "outer portion 42B." The outer portion 42B corresponds to an apex of the equilateral triangle shape. The outer portion 42B is peaked. A length between the inner portion 412A and the outer portion 42B, namely a thickness R12 of the portion at which the second portion 412 of the flexible portion 41 and the hard portion 42 are laminated, is 0.4 mm.

An end surface on the distal end side of the hard portion 42 is referred to as a "distal end surface 42S." A virtual first direction D11 is defined that extends toward the outside along the distal end surface 42S of the hard portion 42. The first direction D11 is inclined toward the proximal end side with respect to a direction orthogonal to the extending direction. An end surface on the proximal end side of the hard portion 42 is referred to as a "proximal end surface 42K." A virtual second direction D12 is defined that extends toward the outside along the proximal end surface 42K of the hard portion 42. The second direction D12 is inclined toward the distal end side with respect to the direction orthogonal to the extending direction. An acute angle, of angles formed between the first direction D11 and the extending direction, is defined as a first angle θ11. The first angle θ11 is an angle between 4 to 13 degrees, for example. The first angle θ11 is preferably 5 degrees. An acute angle, of angles formed between the second direction D12 and the extending direction, is defined as a second angle θ12. The second angle θ12 is an angle between 5 to 16 degrees, for example. The second angle θ12 is preferably 16 degrees. The preferable five degrees of the first angle θ11 is smaller than the preferable sixteen degrees of the second angle θ12.

As shown in FIG. 7, when the balloon 3 is in the inflated state, a position of a boundary on the distal end side of the second portion 412 of the flexible portion 41, namely, a position of a boundary between the second portion 412 and the third portion 413, is aligned, in the extending direction, with the position P11 of the end portion on the distal end side of the marker 22A. A position of a boundary on the proximal end side of the second portion 412 of the flexible portion 41, namely, a position of a boundary between the first portion 411 and the second portion 412, is aligned, in the extending direction, with the position P21 of the end portion on the proximal end side of the marker 22B.

As described above, the boundary on the distal end side of the inflatable region 33 is aligned, in the extending direction, with the position P11 of the end portion on the distal end side of the marker 22A. The boundary on the proximal end side of the inflatable region 33 is aligned, in the extending direction, with the position P21 of the end portion on the proximal end side of the marker 22B. Thus, when the balloon 3 is in the inflated state, the inflatable region 33 of the balloon 3, the second portion 412 of the flexible portion 41, and the hard portion 42 are all disposed in the same position in the extending direction. The second portion 412 of the flexible portion 41 is disposed along the outer peripheral surface of the inflatable region 33 of the balloon 3. The inner portion 412A of the second portion 412 of the flexible portion 41 faces the inflatable region 33 of the balloon 3. The hard portion 42 is disposed on the opposite side to the portion facing the inflatable region 33 of the balloon 3, namely, on the opposite side to the inner portion 412A of the second portion 412 of the flexible portion 41.

The linear member 4 is formed of a polyamide resin. More specifically, the flexible portion 41 is formed of a polyamide elastomer. The hardness of the flexible portion 41 is a value within a range of D25 to D63 as prescribed in ISO 868. The hard portion 42 is formed of a polyamide resin. The hardness of the hard portion 42 is a value within a range of D70 to D95 as prescribed in ISO 868. The flexible portion 41 is softer than the hard portion 42. In comparison to the hard portion 42, the flexible portion 41 has excellent extendability.

A state of the linear member 4 when the balloon 3 inflates as a result of the compressed fluid being supplied from the hub 5 will be explained. In accordance with the inflation of the balloon 3, the hard portion 42 of the linear member 4 separates from the protruding portion 225 of the inner tube 22 (refer to FIG. 7). At that time, of the flexible portion 41 of the linear member 4, the first portion 411 and the third portion 413 elastically deform so as to extend along the extending direction, while the second portion 412 on which the hard portion 42 is laminated does not. As a result, the hard portion 42 easily separates from the protruding portion 225 of the inner tube 22. The inner surface 412A of the second portion 412 of the flexible portion 41 is disposed along the outer peripheral surface of the inflatable region 33 of the balloon 3. The outer portion 42B (refer to FIG. 8) of the hard portion 42 protrudes to the outside from the outer portion 412B of the second portion 412 of the flexible portion 41 (refer to FIG. 6). As described above, in comparison to the flexible portion 41, the hard portion 42 does not easily extend. Thus, even when the balloon 3 inflates, the second portion 412 of the flexible portion 41 of the linear member 4 does not extend to the same extent as the first portion 411 and the third portion 413 of the flexible portion 41.

A state of the linear member 4 when the balloon 3 deflates as a result of the compressed fluid being discharged from the balloon 3 in the inflated state will be explained. When the balloon 3 is deflated, the first portion 411 and the third portion 413 of the flexible portion 41 of the linear member 4 that have extended in the extending direction contract due to the restoring force. The hard portion 42 of the linear member 4 approaches the protruding portion 225 of the inner tube 22 (refer to FIG. 4). Warping of the linear member 4 is suppressed by the contraction of the first portion 411 and the third portion 413 of the flexible portion 41. The linear member 4A is covered from the outside by the pleat 3A. The linear member 4B is covered from the outside by the pleat 3B. The linear member 4C is covered from the outside by the pleat 3C (refer to FIG. 3).

As long as the flexible portion 41 and the hard portion 42 of the linear member 4 have favorable hardness and extendability, the material thereof is not limited to the polyamide resin, and another synthetic resin can be used. The material is not limited to the synthetic resin, and stainless steel, a Ni—Ti alloy, or carbon fiber may be used.

Main Operations and Effects of First Embodiment

In the balloon catheter 10 of the first embodiment, when the balloon 3 inflates, since the inflatable region 33 moves to the outside, the hard portion 42 of the linear member 4 that is disposed along the outer peripheral surface of the inflatable region 33 also tries to move to the outside. In response to this, of the flexible portion 41 of the linear member 4, the first portion 411 and the third portion 413 on which the hard portion 42 is not laminated elastically deform so as to extend along the extending direction. As a result, the hard portion 42 can easily move to the outside. The outer portion 42B of the hard portion 42 of the linear member 4 protrudes to the outside from the outer portion 412B on the opposite side to the inner portion 412A that faces the outer peripheral surface of the balloon 3. The hard portion 42 has a higher hardness than the flexible portion 41. Thus, in a state in which the balloon 3 is disposed in a constricted portion of a blood vessel, when the balloon 3 is inflated, the hard portion 42 acts appropriately on the constricted portion of the blood vessel. For example, the hard portion 42 is peaked at the outer portion 42B, and thus the hard portion 42 can easily bite into a lesioned part (not shown in the drawings) of the blood vessel. As a result, in a state in which the linear member 4 causes the balloon 3 to be in a state of not easily slipping with respect to the lesioned part of the blood vessel, the lesioned part can be expanded from the inside by the inflation of the balloon 3.

In the balloon catheter 10, the first portion 411 and the third portion 413 of the flexible portion 41 are caused to extend in accordance with the inflation of the balloon 3, and the hard portion 42 is caused to move to the outside. In this way, the balloon catheter 10 can cause the hard portion 42 to act on the constricted portion inside the blood vessel. As a result, other than the linear members 4, the balloon catheter 10 does not require a member that is necessary to be able to move the hard portion 42 to the outside. Thus, when a user tries to move the balloon 3 as far as the constricted portion of the blood vessel, the balloon catheter 10 can inhibit obstruction of the movement of the balloon 3 by the member other than the linear members 4. In this way, the balloon catheter 10 can cause the balloon 3 to appropriately approach and be disposed at the constricted portion of the blood vessel.

The flexible portion 41 of the linear member 4 extends between the distal end position M1 and the proximal end position M2. Of the flexible portion 41, the hard portion 42 is laminated on the second portion 412 that is disposed along the outer peripheral surface of the inflatable region 33 in the inflated state. When the balloon 3 is in the inflated state, the hard portion 42 protrudes to the outside from the outer portion 412B of the second portion 412 of the flexible portion 41. Thus, the balloon catheter 10 can inhibit the hard portion 42 from obstructing the extending of the first portion 411 and the third portion 413 of the flexible portion 41, on which the hard portion 42 is not laminated. The flexible portion 41 extends appropriately at the first portion 411 and the third portion 413. Thus, the balloon catheter 10 can easily move the hard portion 42 to the outside in accordance with the inflation of the balloon 3.

The first direction D11, which extends to the outside along the distal end surface 42S that is the end portion of the hard portion 42 on the distal end side, is inclined toward the proximal end side. In this case, when the balloon catheter 10 moves inside the blood vessel in the course of the user causing the balloon 3 to approach the constricted portion of the blood vessel, the linear member 4 can be inhibited from catching on the inner wall of the blood vessel. Thus, the user can smoothly move the balloon 3 as far as the constricted portion of the blood vessel. Further, the second direction D12, which extends to the outside along the proximal end surface 42K that is the end portion of the hard portion 42 on the proximal end side, is inclined toward the distal end side. In this case, when the balloon catheter 10 moves inside the blood vessel in the course of the user pulling the balloon catheter 10 out from the blood vessel, the linear member 4 can be inhibited from catching on the inner wall of the blood vessel. Thus, the user can easily pull the balloon catheter 10 out from the blood vessel.

With respect to the flexible portion 41, the thickness R13 of the third portion 413 located further toward the distal end side than the hard portion 42 is narrower than the thickness R11 of the first portion 411 located further toward the proximal end side than the hard portion 42. In this case, in comparison to a case in which the thickness R13 is thicker than the thickness R11, or a case in which the thicknesses R11 and R13 are the same as each other, the balloon catheter 10 can make the diameter of the distal end portion smaller. Thus, the user can cause the balloon 3 of the balloon catheter 10 to move as far as the constricted portion of the blood vessel using less force.

The first angle θ11, which is the acute angle of the angles formed between the extending direction and the first direction D11, is smaller than the second angle θ12, which is the acute angle of the angles formed between the extending direction and the second direction D12. In this case, the balloon catheter 10 can use the portion of the distal end surface 42S to reduce a rate of change of the hardness in the extending direction of the linear member 4. Further, since the first angle θ11 is small, the balloon catheter 10 can inhibit the linear members 4 from catching on the inner wall of the blood vessel when the user moves the balloon catheter 10 as far as the constricted portion inside the blood vessel. In this way, the user can easily move the balloon 3 as far as the constricted portion of the blood vessel.

The protruding portion 225 of the inner tube 22 is provided with the markers 22A and 22B in the positions separated from each other in the extending direction. The position P11 of the distal end side of the distal end side marker 22A is aligned with the position of the boundary of the distal end side of the inflatable region 33. The position P21 of the proximal end side of the proximal end side marker 22B is aligned with the position of the boundary of the proximal end side of the inflatable region 33. In this case, the user can correctly determine the inflatable region 33 when the balloon 3 is inflated, using the markers 22A and 22B. Further, the hard portion 42 is disposed so as to correspond to the inflatable region 33 identified by the markers 22A and 22B. Thus, the user can easily ascertain that the hard portion 42 of the linear member 4 is acting appropriately on the blood vessel at the inflatable region 33 identified by the markers 22A and 22B.

The proximal end side leg portion 31 of the balloon 3 is connected to the outer tube 21 further toward the distal end side than the proximal end position M2. The proximal end position M2 corresponds to the position at which the end portion on the proximal end side of the linear member 4 is connected to the outer tube 21 via the mounting member 21A. Thus, the balloon catheter 10 can cause the linear member 4 to be separated from the end portion on the proximal end side of the balloon 3. In this case, the end portion on the proximal end side of the linear member 4 is strongly fixed to the outer tube 21. Further, the balloon catheter 10 can suppress an impact on the proximal end side leg portion 31 of the balloon 3 caused by tension acting on the linear member 4.

The linear member 4 is formed of the synthetic resin. In this case, the linear member 4 that includes the flexible portion 41 and the hard portion 42 can easily be manufactured by injection molding, extrusion molding or the like.

Second Embodiment

A balloon catheter 20 according to a second embodiment of the present disclosure will be explained with reference to FIG. 9. Points in which the second embodiment differs from the first embodiment are as follows:

The mounting member 21A (refer to FIG. 2 and the like) is not mounted on the outer tube 21, and The end portion on the proximal end side of the linear member 4 is connected further toward the proximal end side than the center in the extending direction of the proximal end side leg portion 31 of the balloon 3.

Hereinafter, where the configuration is the same as that of the first embodiment, the same reference numerals are assigned and an explanation thereof is omitted.

Figure 9:
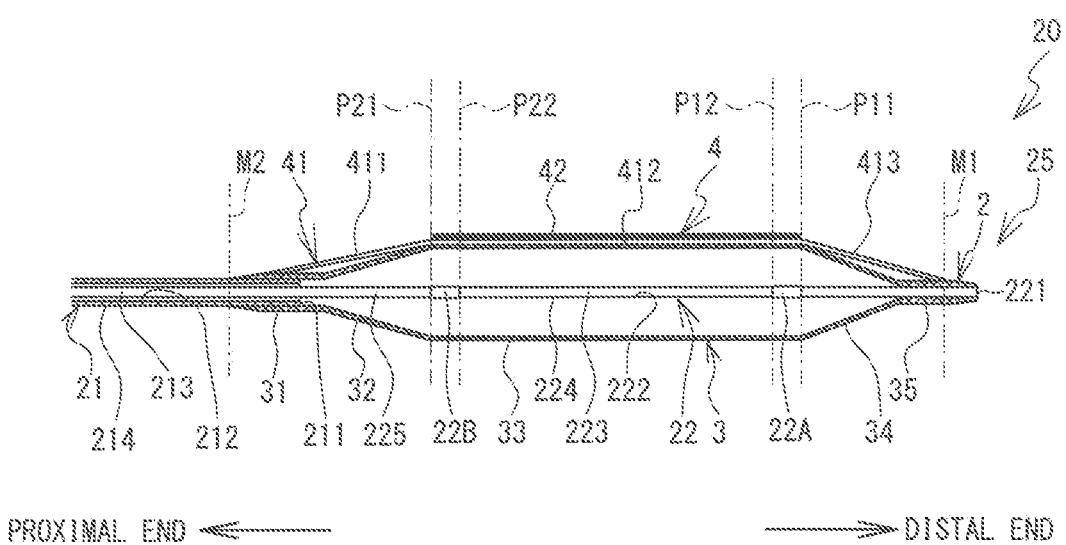
FIG. 9 is a cross-sectional view of the balloon and the linear member according to a second embodiment.

As shown in FIG. 9, the end portion on the proximal end side of the linear member 4 is connected, by thermal welding, further toward the proximal end side than the center in the extending direction of the outer peripheral surface of the proximal end side leg portion 31 of the balloon 3. The proximal end position M2 that shows the position at which the end portion on the proximal end side of the linear member 4 is connected corresponds to a position, of the proximal end side leg portion 31 of the balloon 3, which is located further toward the proximal end side than the center in the extending direction.

Main Operations and Effects of Second Embodiment

In the balloon catheter 20 according to the second embodiment, the linear member 4 can be fixed to the outer tube 21 without needing the mounting member 21A. Thus, the costs of the balloon catheter 10 can be reduced. Further, in comparison to a case in which the linear member 4 is connected directly to the outer tube 21, the linear member 4 can be reliably connected to the outer tube 21 by connecting the linear member 4 to the outer tube 21 via the balloon 3.

Third Embodiment

A balloon catheter 30 according to a third embodiment of the present disclosure will be explained with reference to FIG. 10 and FIG. 11. A point in which the third embodiment differs from the second embodiment is that a linear member 6 is provided in place of the linear member 4. Hereinafter, where the configuration is the same as that of the first embodiment and the second embodiment, the same reference numerals are assigned and an explanation thereof is omitted.

Figure 10:
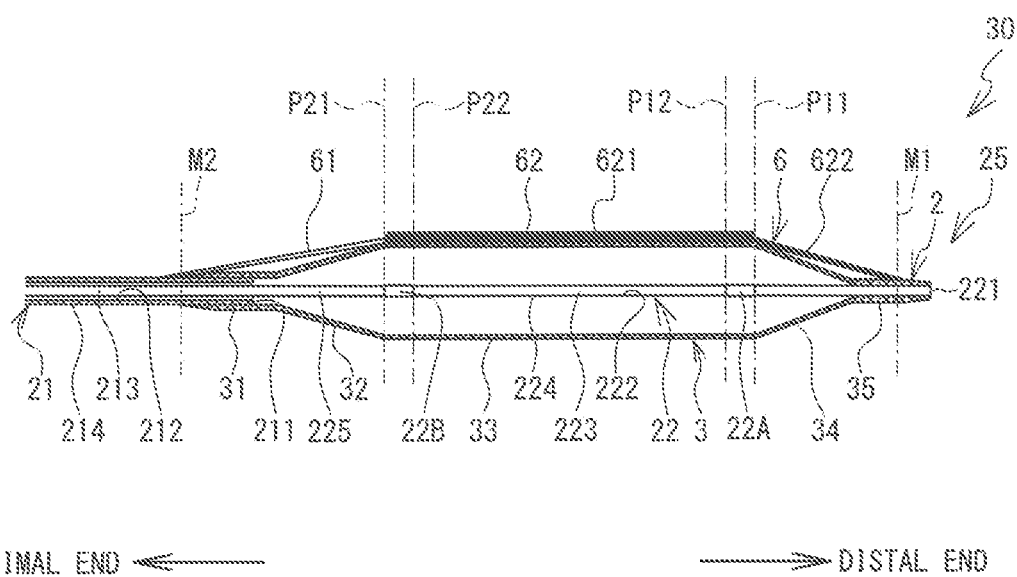
FIG. 10 is a cross-sectional view of the balloon and a linear member according to a third embodiment.

As shown in FIG. 10, the linear member 6 includes a flexible portion 61, and a hard portion 62. The end portion on the proximal end side of the flexible portion 61 is connected to the outer peripheral surface of the proximal end side leg portion 31 of the balloon 3, at the proximal end position M2. The hard portion 62 includes a first portion 621 and a second portion 622. The first portion 621 is adjacent to the distal end side of the flexible portion 61. The second portion 622 is adjacent to the distal end side of the first portion 621. The end portion on the distal end side of the second portion 622 is connected to the outer peripheral surface of the distal end side leg portion 35 of the balloon 3, at the distal end position M1. The flexible portion 61, the first portion 621 of the hard portion 62, and the second portion 622 of the hard portion 62 are disposed side by side in that order from the proximal end toward the distal end along the extending direction.

The flexible portion 61 corresponds to the first portion 411 (refer to FIG. 8) of the flexible portion 41 according to the first embodiment. The first portion 621 of the hard portion 62 corresponds to the laminated portion (refer to FIG. 8) according to the first embodiment, in which the second portion 412 of the flexible portion 41 and the hard portion 42 are laminated. The second portion 622 of the hard portion 62 corresponds to the third portion 413 (refer to FIG. 8) of the flexible portion 41 according to the first embodiment. The shape of each of the portions is the same. The material of the flexible portion 61 is the same as the material of the flexible portion 41 according to the first embodiment. The material of the hard portion 62 is the same as the material of the hard portion 42 according to the first embodiment.

Figure 11:
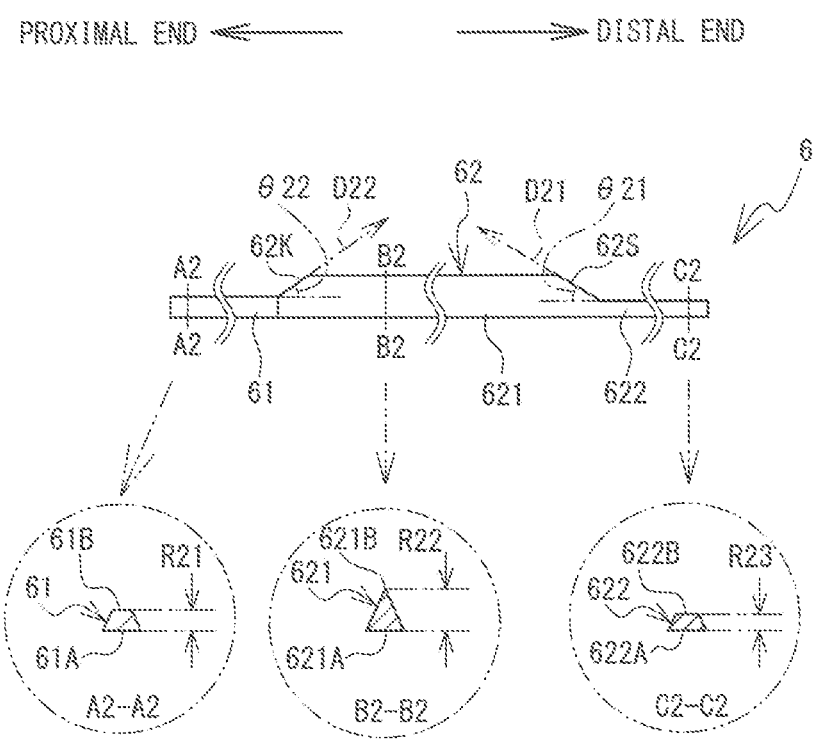
FIG. 11 shows a side view and cross-sectional views of the linear member.

FIG. 11 shows cross sections of the linear member 6 at each of a line A2-A2, a line B2-B2, and a line C2-C2. The shape of the cross section of the flexible portion 61 is a trapezoid shape. An inner portion 61A and an outer portion 61B respectively correspond to the inner portion 411A and the outer portion 411B (refer to FIG. 8) of the flexible portion 41. A length between the inner portion 61A and the outer portion 61B of the flexible portion 61, namely, a thickness R21 of the flexible portion 61, is the same as the thickness R11 in the linear member 4. The shape of the cross section of the first portion 621 of the hard portion 62 is an equilateral triangle shape. An inner portion 621A and an outer portion 621B respectively correspond to the inner portion 412A and the outer portion 42B (refer to FIG. 8) of the flexible portion 41. A length between the inner portion 621A and the outer portion 621B, namely, a thickness R22 of the first portion 621 of the hard portion 62, is the same as the thickness R12 in the linear member 4. The shape of the cross section of the second portion 622 of the hard portion 62 is a trapezoid shape. An inner portion 622A and an outer portion 622B respectively correspond to the inner portion 413A and the outer portion 413B (refer to FIG. 8) of the flexible portion 41. A length between the inner portion 622A and the outer portion 622B of the hard portion 62, namely, a thickness R23 of the second portion 622, is the same as the thickness R13 in the linear member 4. A distal end surface 62S and a proximal end surface 62K respectively correspond to the distal end surface 42S and the proximal end surface 42K (refer to FIG. 8) of the hard portion 42. A first direction D21 and a second direction D22 respectively correspond to the first direction D11 and the second direction D12 (refer to FIG. 8). A first angle θ21 and a second angle θ22 respectively correspond to the first angle θ11 and the second angle θ12 (refer to FIG. 8). The preferable five degrees of the first angle θ21 is smaller than the preferable sixteen degrees of the second angle θ22.

In accordance with the inflation of the balloon 3, the first portion 621 of the hard portion 62 of the linear member 6 tries to move away from the protruding portion 225 of the inner tube 22. At this time, the flexible portion 61 of the linear member 6 elastically deforms so as to extend along the extending direction. Thus, the first portion 621 of the hard portion 62 easily separates from the protruding portion 225 of the inner tube 22. The outer portion 621B of the first portion 621 of the hard portion 62 protrudes to the outside with respect to the balloon 3.

Main Operations and Effects of Third Embodiment

In the balloon catheter 30 according to the third embodiment, the first portion 621 of the hard portion 62 is disposed in a portion, of the linear member 6, that is aligned with the position, in the extending direction, of the inflatable region 33 of the balloon 3 in the inflated state. When the balloon 3 is inflated, the flexible portion 61 of the linear member 6 elastically deforms so as to extend along the extending direction. In this way, the first portion 621 of the hard portion 62 moves away from the protruding portion 225 of the inner tube 22. The outer portion 621B is disposed on the opposite side to the inner portion 621A that faces the outer peripheral surface of the balloon 3. Thus, with the balloon catheter 30, when the balloon 3 is inflated in the state in which the balloon 3 is disposed at the constricted portion of the blood vessel, the hard portion 62 acts appropriately on the constricted portion of the blood vessel.

In the balloon catheter 30, the first portion 621 of the hard portion 62 is provided from the inside, which faces the inflatable region 33 of the balloon 3, to the outside. Thus, even if the linear member 6 rotates with respect to the balloon 3, the linear member 6 can orient the hard portion 62 toward the outside. Further, the hard portion 62 is disposed not only at the portion corresponding to the inflatable region 33 of the balloon 3, but also at the portion corresponding further toward the distal end side than the inflatable region 33. Thus, the balloon catheter 30 can cause the second portion 622 of the hard portion 62 to act on the constricted portion of the blood vessel further toward the distal end side than the inflatable region 33, when the balloon 3 is inflated in the state in which the balloon 3 is disposed at the constricted portion of the blood vessel.

In the linear member 6, the flexible portion 61 and the hard portion 62 are adjacent in the extending direction. Thus, the linear member 6 can be easily manufactured by connecting the respective end portions of the flexible portion 61 and the hard portion 62 in the extending direction.

Fourth Embodiment

A balloon catheter 40 according to a fourth embodiment of the present disclosure will be explained with reference to FIG. 12 and FIG. 13. A point in which the fourth embodiment differs from the second embodiment is that a linear member 7 is provided in place of the linear member 4. Hereinafter, where the configuration is the same as that of the first embodiment to the third embodiment, the same reference numerals are assigned and an explanation thereof is omitted.

Figure 12:
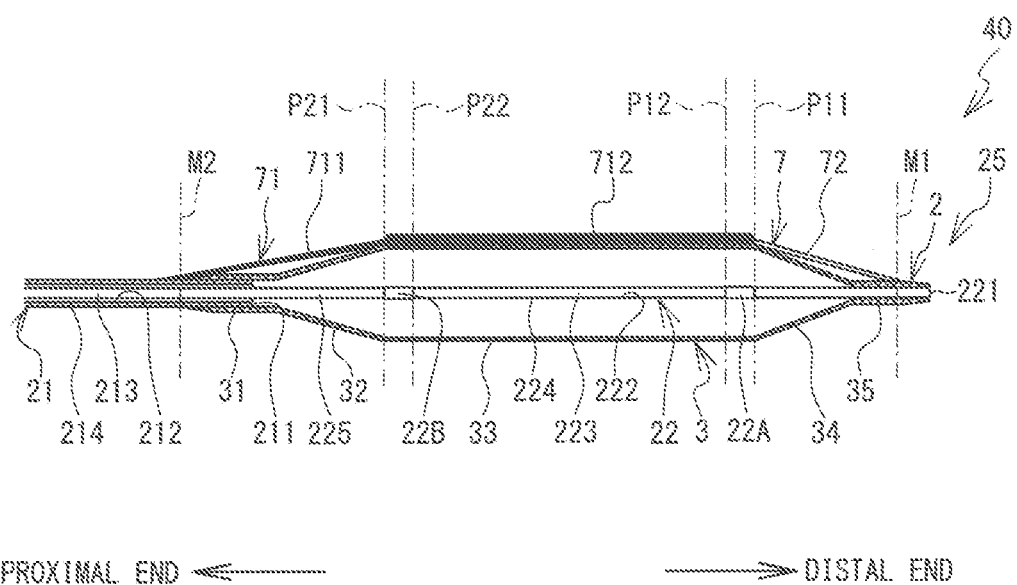
FIG. 12 is a cross-sectional view of the balloon and a linear member according to a fourth embodiment.

As shown in FIG. 12, the linear member 7 includes a hard portion 71 and a flexible portion 72. The hard portion 71 includes a first portion 711 and a second portion 712. The end portion on the proximal end side of the first portion 711 is connected to the outer peripheral surface of the proximal end side leg portion 31 of the balloon 3, at the proximal end position M2. The second portion 712 is adjacent to the distal end side of the first portion 711. The flexible portion 72 is adjacent to the distal end side of the second portion 712 of the hard portion 71. The end portion on the distal end side of the flexible portion 72 is connected to the outer peripheral surface of the distal end side leg portion 35 of the balloon 3, at the distal end position M1. The first portion 711 of the hard portion 71, the second portion 712 of the hard portion 71, and the flexible portion 72 are disposed side by side in that order from the proximal end toward the distal end along the extending direction.

The first portion 711 of the hard portion 71 corresponds to the first portion 411 (refer to FIG. 8) of the flexible portion 41 according to the first embodiment. The second portion 712 of the hard portion 71 corresponds to the laminated portion (refer to FIG. 8) according to the first embodiment, in which the second portion 412 of the flexible portion 41 and the hard portion 42 are laminated. The flexible portion 72 corresponds to the third portion 413 (refer to FIG. 8) of the flexible portion 41 according to the first embodiment. The shape of each of the portions is the same. The material of the flexible portion 72 is the same as the material of the flexible portion 41 according to the first embodiment. The material of the hard portion 71 is the same as the material of the hard portion 42 according to the first embodiment.

Figure 13:
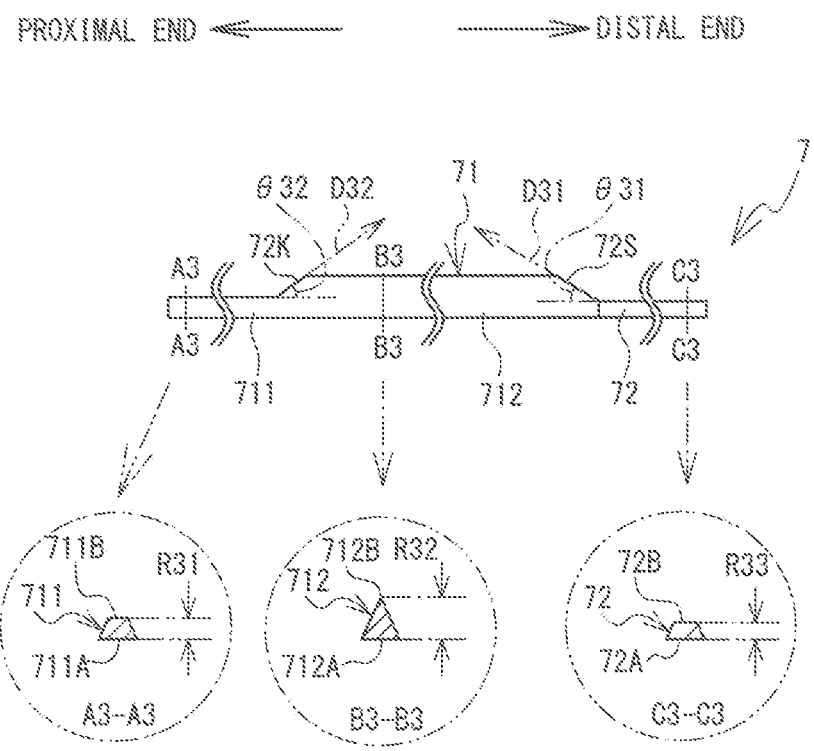
FIG. 13 shows a side view and cross-sectional views of the linear member.

FIG. 13 shows cross sections of the linear member 7 at each of a line A3-A3, a line B3-B3, and a line C3-C3. The cross-sectional shape of the first portion 711 of the hard portion 71 is a trapezoid shape. An inner portion 711A and an outer portion 711B of the first portion 711 respectively correspond to the inner portion 411A and the outer portion 411B (refer to FIG. 8) of the flexible portion 41. A length between the inner portion 711A and the outer portion 711B, namely, a thickness R31 of the first portion 711, is the same as the thickness R11 in the linear member 4. The shape of the cross section of the second portion 712 of the hard portion 71 is an equilateral triangle shape. An inner portion 712A and an outer portion 712B of the second portion 712 respectively correspond to the inner portion 412A and the outer portion 42B (refer to FIG. 8) of the flexible portion 41. A length between the inner portion 712A and the outer portion 712B, namely, a thickness R32 of the second portion 712, is the same as the thickness R12 in the linear member 4. The shape of the cross section of the flexible portion 72 is a trapezoid shape. An inner portion 72A and an outer portion 72B of the flexible portion 72 respectively correspond to the inner portion 413A and the outer portion 413B (refer to FIG. 8) of the flexible portion 41. A length between the inner portion 72A and the outer portion 72B, namely, a thickness R33 of the flexible portion 72, is the same as the thickness R13 in the linear member 4. A distal end surface 72S and a proximal end surface 72K respectively correspond to the distal end surface 42S and the proximal end surface 42K (refer to FIG. 8) of the hard portion 42. A first direction D31 and a second direction D32 respectively correspond to the first direction D11 and the second direction D12 (refer to FIG. 8). A first angle θ31 and a second angle θ32 respectively correspond to the first angle θ11 and the second angle θ12 (refer to FIG. 8). The preferable five degrees of the first angle θ31 is smaller than the preferable sixteen degrees of the second angle θ32.

In accordance with the inflation of the balloon 3, the second portion 712 of the hard portion 71 of the linear member 7 tries to move away from the protruding portion 225 of the inner tube 22. At this time, the flexible portion 72 of the linear member 7 elastically deforms so as to extend along the extending direction. Thus, the second portion 712 of the hard portion 71 easily separates from the protruding portion 225 of the inner tube 22. The outer portion 712B of the second portion 712 of the hard portion 71 protrudes to the outside with respect to the balloon 3.

Main Operations and Effects of Fourth Embodiment

In the balloon catheter 40 according to the fourth embodiment, the second portion 712 of the hard portion 71 is disposed in a portion, of the linear member 7, that is aligned with the position, in the extending direction, of the inflatable region 33 of the balloon 3 in the inflated state. When the balloon 3 is inflated, the flexible portion 72 of the linear member 7 elastically deforms so as to extend along the extending direction. In this way, the second portion 712 of the hard portion 71 moves away from the protruding portion 225 of the inner tube 22. The outer portion 712B is disposed on the opposite side to the inner portion 712A that faces the outer peripheral surface of the balloon 3. Thus, with the balloon catheter 40, when the balloon 3 is inflated in the state in which the balloon 3 is disposed at the constricted portion of the blood vessel, the hard portion 71 acts appropriately on the constricted portion of the blood vessel.

In the balloon catheter 40, the second portion 712 of the hard portion 71 is provided from the inside, which faces the inflatable region 33 of the balloon 3, to the outside. Thus, even if the linear member 7 rotates with respect to the balloon 3, the linear member 7 can orient the hard portion 71 toward the outside. Further, the hard portion 71 is disposed not only at the portion corresponding to the inflatable region 33 of the balloon 3, but also at the portion corresponding further toward the proximal end side than the inflatable region 33. Thus, the balloon catheter 40 can cause the first portion 711 of the hard portion 71 to act on the constricted portion of the blood vessel further toward the proximal end side than the inflatable region 33, when the balloon 3 is inflated in the state in which the balloon 3 is disposed at the constricted portion of the blood vessel.

In the linear member 7, the hard portion 71 and the flexible portion 72 are adjacent in the extending direction. Thus, the linear member 7 can be easily manufactured by connecting the respective end portions of the hard portion 71 and the flexible portion 72 in the extending direction.

Fifth Embodiment

A balloon catheter 50 according to a fifth embodiment of the present disclosure will be explained with reference to FIG. 14 and FIG. 15. A point in which the fifth embodiment differs from the second embodiment is that a linear member 8 is provided in place of the linear member 4. Hereinafter, where the configuration is the same as that of the first embodiment to the fourth embodiment, the same reference numerals are assigned and an explanation thereof is omitted.

Figure 14:
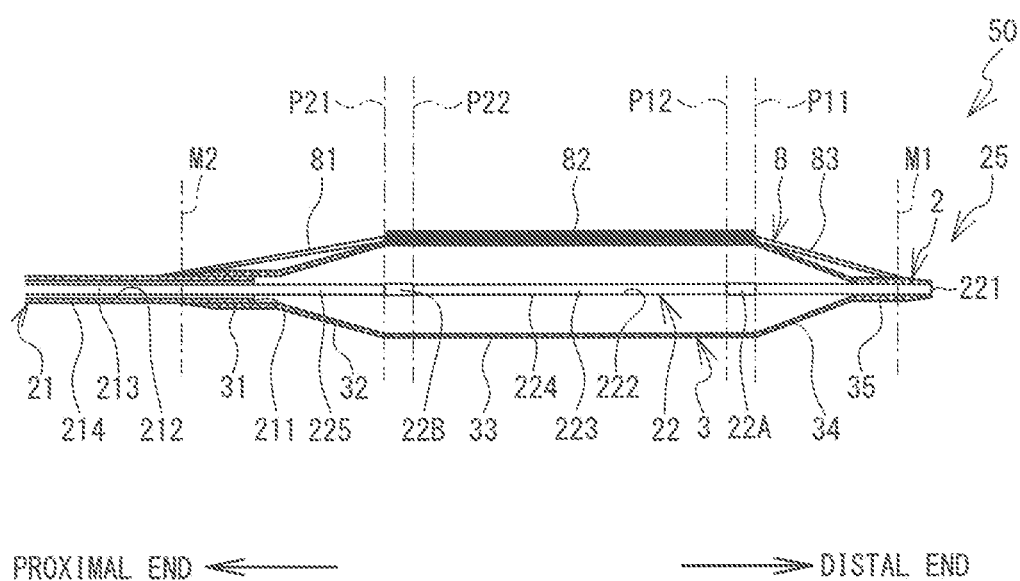
FIG. 14 is a cross-sectional view of the balloon and a linear member according to a fifth embodiment.

As shown in FIG. 14, the linear member 8 includes flexible portions 81 and 83, and a hard portion 82. The end portion on the proximal end side of the flexible portion 81 is connected to the outer peripheral surface of the proximal end side leg portion 31 of the balloon 3, at the proximal end position M2. The hard portion 82 is adjacent to the distal end side of the flexible portion 81. The flexible portion 83 is adjacent to the distal end side of the hard portion 82. The end portion on the distal end side of the flexible portion 83 is connected to the outer peripheral surface of the distal end side leg portion 35 of the balloon 3, at the distal end position M1. The flexible portion 81, the hard portion 82, and the flexible portion 83 are disposed side by side in that order from the proximal end toward the distal end along the extending direction.

The flexible portion 81 corresponds to the first portion 411 (refer to FIG. 8) of the flexible portion 41 according to the first embodiment. The hard portion 82 corresponds to the laminated portion (refer to FIG. 8) according to the first embodiment, in which the second portion 412 of the flexible portion 41 and the hard portion 42 are laminated. The flexible portion 83 corresponds to the third portion 413 (refer to FIG. 8) of the flexible portion 41 according to the first embodiment. The shape of each of the portions is the same. The material of the flexible portions 81 and 83 is the same as the material of the flexible portion 41 according to the first embodiment. The material of the hard portion 82 is the same as the material of the hard portion 42 according to the first embodiment.

Figure 15:
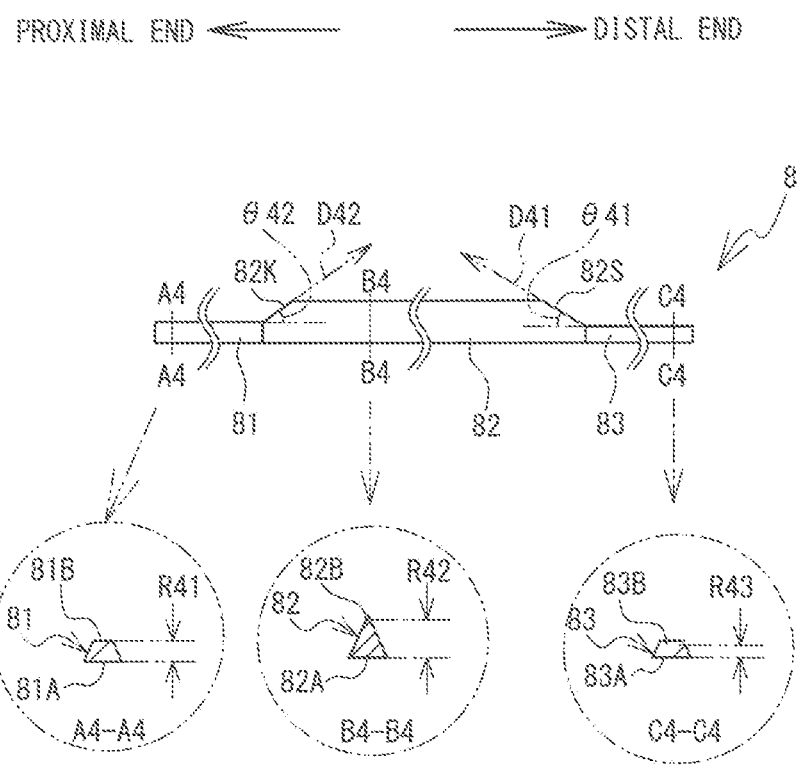
FIG. 15 shows a side view and cross-sectional views of the linear member.

FIG. 15 shows cross sections of the linear member 8 at each of a line A4-A4, a line B4-B4, and a line C4-C4. The cross-sectional shape of the flexible portion 81 is a trapezoid shape. An inner portion 81A and an outer portion 81B of the flexible portion 81 respectively correspond to the inner portion 411A and the outer portion 411B (refer to FIG. 8) of the flexible portion 41. A length between the inner portion 81A and the outer portion 81B, namely, a thickness R41 of the flexible portion 81, is the same as the thickness R11 in the linear member 4. The shape of the cross section of the hard portion 82 is an equilateral triangle shape. An inner portion 82A and an outer portion 82B of the hard portion 82 respectively correspond to the inner portion 412A and the outer portion 42B (refer to FIG. 8) of the flexible portion 41. A length between the inner portion 82A and the outer portion 82B, namely, a thickness R42 of the hard portion 82, is the same as the thickness R12 in the linear member 4. The shape of the cross section of the flexible portion 83 is a trapezoid shape. An inner portion 83A and an outer portion 83B of the flexible portion 83 respectively correspond to the inner portion 413A and the outer portion 413B (refer to FIG. 8) of the flexible portion 41. A length between the inner portion 83A and the outer portion 83B, namely, a thickness R43 of the flexible portion 83, is the same as the thickness R13 in the linear member 4. A distal end surface 82S and a proximal end surface 82K respectively correspond to the distal end surface 42S and the proximal end surface 42K (refer to FIG. 8) of the hard portion 42. A first direction D41 and a second direction D42 respectively correspond to the first direction D11 and the second direction D12 (refer to FIG. 8). A first angle θ41 and a second angle θ42 respectively correspond to the first angle θ11 and the second angle θ12 (refer to FIG. 8). The preferable five degrees of the first angle θ41 is smaller than the preferable sixteen degrees of the second angle θ42.

In accordance with the inflation of the balloon 3, the hard portion 82 of the linear member 8 tries to move away from the protruding portion 225 of the inner tube 22. At this time, the flexible portions 81 and 83 of the linear member 8 elastically deform so as to extend along the extending direction. Thus, the hard portion 82 easily separates from the protruding portion 225 of the inner tube 22. The outer portion 82B of the hard portion 82 protrudes to the outside with respect to the balloon 3.

Main Operations and Effects of Fifth Embodiment

In the balloon catheter 50 according to the fifth embodiment, the hard portion 82 is disposed in a portion, of the linear member 8, that is aligned with the position, in the extending direction, of the inflatable region 33 of the balloon 3 in the inflated state. When the balloon 3 is inflated, the flexible portions 81 and 83 of the linear member 8 elastically deform so as to extend along the extending direction. In this way, the hard portion 82 moves away from the protruding portion 225 of the inner tube 22. The outer portion 82B is disposed on the opposite side to the inner portion 82A that faces the outer peripheral surface of the balloon 3. Thus, when the balloon 3 is inflated in the state in which the balloon 3 is disposed at the constricted portion of the blood vessel, the hard portion 82 acts appropriately on the constricted portion of the blood vessel.

In the balloon catheter 50, the flexible portions 81 and 83 are provided on the distal end side and the proximal end side of the hard portion 82. Thus, the linear member 8 easily extends in the extending direction when the balloon 3 is inflated. As a result, the balloon catheter 50 can easily cause the hard portion 82 to separate from the protruding portion 225 of the inner tube 22.

In the linear member 8, the flexible portion 81, the hard portion 82, and the flexible portion 83 are adjacent to each other in the extending direction. Thus, the linear member 8 can be easily manufactured by connecting the respective end portions in the extending direction of the flexible portions 81 and 81, and the hard portion 82.

Sixth Embodiment

A balloon catheter 90 according to a sixth embodiment will be explained with reference to FIG. 16 to FIG. 19. Points in which the sixth embodiment differs from the second embodiment are as follows:
A linear member 9 is provided in place of the linear member 4, and
The linear member 9 is bonded to the balloon 3 across the whole length of the linear member 9 in the extending direction.

Hereinafter, where the configuration is the same as that of the first embodiment to the fifth embodiment, the same reference numerals are assigned and an explanation thereof is omitted.

Linear Member 9

Figure 16:
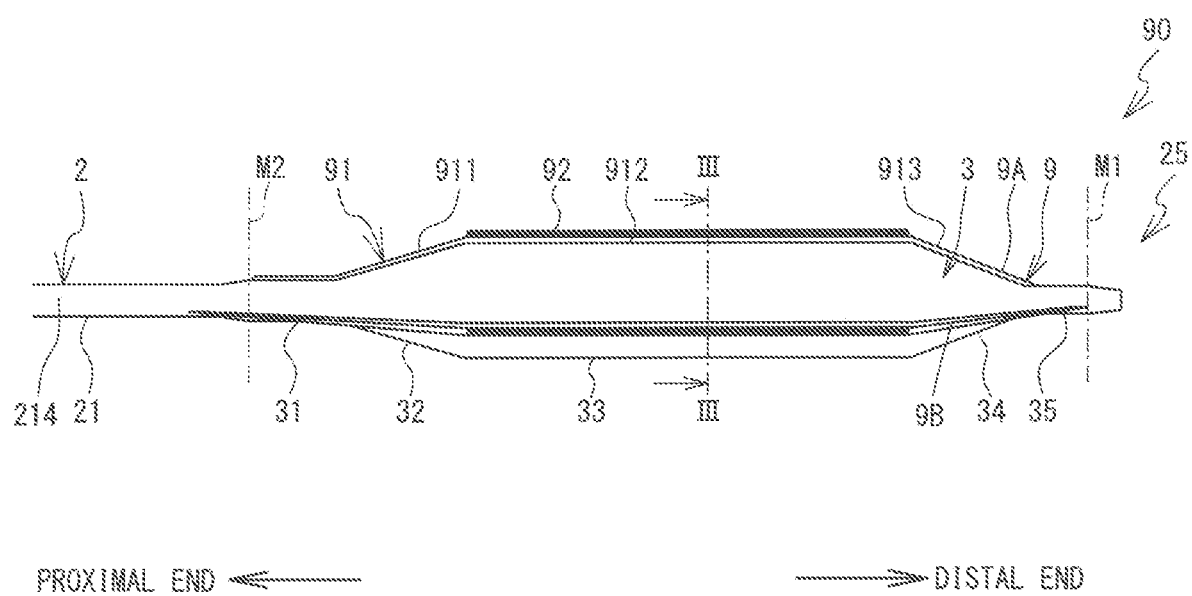
FIG. 16 is a side view of the balloon and a linear member according to a sixth embodiment.
Figure 17:
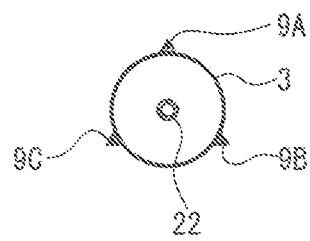
FIG. 17 is a cross-sectional view in the direction of arrows along a line III-III shown in FIG. 16.
Figure 18:
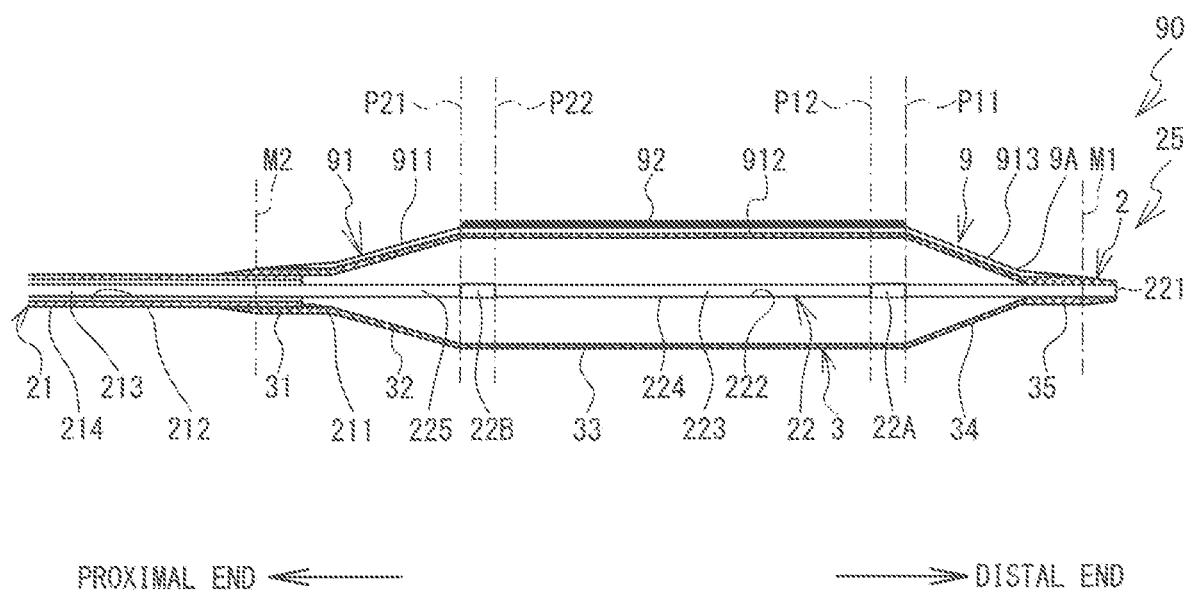
FIG. 18 is a cross-sectional view of the balloon and the linear member in the inflated state.

The linear member 9 will be explained with reference to FIG. 16 to FIG. 19. Linear members 9A, 9B, and 9C respectively correspond to the linear members 4A, 4B, and 4C according to the second embodiment. As shown in FIG. 16 to FIG. 18, the linear member 9 is bonded to the outer peripheral surface of the balloon 3 across the whole length of the linear member 9 from the proximal end position M2 to the distal end position M1. For example, the linear member 9 is bonded to the outer peripheral surface of the balloon 3 using thermal welding. However, the linear member 9 may be bonded to the outer peripheral surface of the balloon 3 using another method, such as adhesive or the like. As shown in FIG. 17, when the balloon 3 is in the inflated state, the linear members 9A, 9B, and 9C extend in straight lines in the extending direction, at positions respectively dividing the balloon 3 into three approximately equal parts in the circumferential direction. At that time, a force in a direction to try and elongate the linear member 9 in the extending direction (hereinafter referred to as a "force in an elongation direction") acts on the linear member 9. In contrast to this, when the balloon 3 is in the deflated state, the force in the elongation direction does not act on the linear member 9.

As shown in FIG. 16 and FIG. 18, the linear member 9 includes a flexible portion 91 and a hard portion 92. The flexible portion 91 extends between the proximal end position M2 and the distal end position M1. The flexible portion 91 includes a first portion 911, a second portion 912, and a third portion 913. The first portion 911, the second portion 912, and the third portion 913 respectively correspond to sections of the flexible portion 91 that is divided into three in the extending direction. The first portion 911 is bonded to the outer peripheral surfaces of the proximal end side leg portion 31 and the proximal end side cone region 32 of the balloon 3. The second portion 912 is adjacent to the distal end side of the first portion 911. The second portion 912 is bonded to the outer peripheral surface of the inflatable region 33 of the balloon 3. The third portion 913 is adjacent to the distal end side of the second portion 912. The third portion 913 is bonded to the outer peripheral surfaces of the distal end side cone region 34 and the distal end side leg portion 35 of the balloon 3. The hard portion 92 is laminated to a portion, of the second portion 912 of the flexible portion 91, on the opposite side to the portion bonded to the balloon 3.

Figure 19:
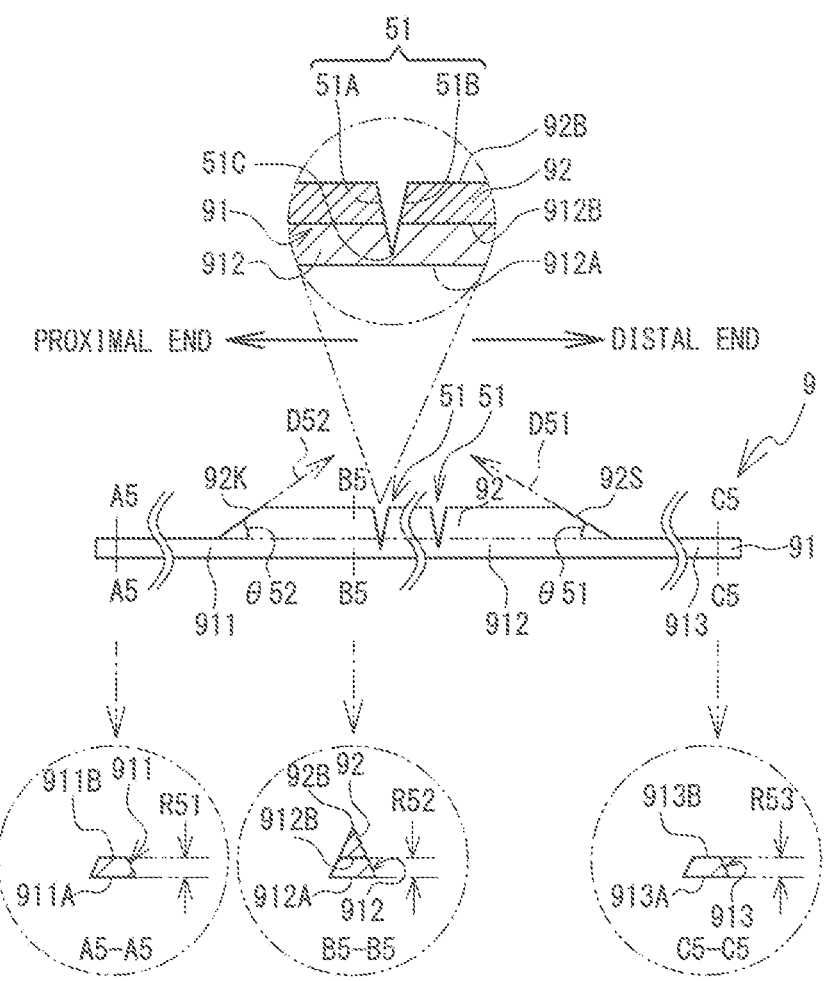
FIG. 19 shows a side view and cross-sectional views of the linear member.

FIG. 19 shows cross sections of the linear member 9 at each of a line A5-A5, a line B5-B5, and a line C5-C5 in a state in which the force in the elongation direction is not acting on the linear member 9. The cross-sectional shape of the linear member 9 is a trapezoid shape or an equilateral triangle shape. Specifically, it is as described below.

The shape of the cross section of the flexible portion 91 (the first portion 911 to the third portion 913) is the trapezoid shape. Hereinafter, of the first portion 911 of the flexible portion 91, a portion bonded to the balloon 3 (refer to FIG. 16) is referred to as an "inner portion 911A." Of the first portion 911, a portion on the opposite side to the inner portion 911A is referred to as an "outer portion 911B." Of the second portion 912 of the flexible portion 91, a portion bonded to the balloon 3 is referred to as an "inner portion 912A." Of the second portion 912, a portion on the opposite side to the inner portion 912A is referred to as a "boundary 912B." Of the third portion 913 of the flexible portion 91, a portion bonded to the balloon 3 is referred to as an "inner portion 913A." Of the third portion 913, a portion on the opposite side to the inner portion 913A is referred to as an "outer portion 913B." The inner portions 911A, 912A, and 913A respectively correspond to the lower base of the trapezoid that is the cross-sectional shape. The outer portions 911B and 913B, and the boundary 912B respectively correspond to the upper base of the trapezoid that is the cross-sectional shape.

The shape of the cross section of the hard portion 92 is an equilateral triangle shape having the boundary 912B of the second portion 912 as one side. The hard portion 92 protrudes to the outside from the boundary 912B of the second portion 912 of the flexible portion 91. Hereinafter, an end portion on the outside of the hard portion 92 is referred to as an "outer portion 92B." The outer portion 92B corresponds to an apex of the equilateral triangle shape, and thus is peaked.

A length between the inner portion 911A and the outer portion 911B of the first portion 911, namely, a thickness of a portion of the flexible portion 91 further toward the proximal end side than the hard portion 92, is denoted as a thickness R51. A length between the inner portion 912A and the boundary 912B of the second portion 912, namely, a thickness of a portion of the flexible portion 91 that overlaps with the hard portion 92 in the extending direction, is denoted as R52. A length between the inner portion 913A and the outer portion 913B of the third portion 913, namely, a thickness of a portion of the flexible portion 91 further toward the distal end side than the hard portion 92, is denoted as R53. In this case, the thicknesses R51, R52, and R53 are equal.

An end surface on the distal end side of the hard portion 92 is referred to a "distal end surface 92S." A virtual first direction D51 is defined that extends toward the outside along the distal end surface 92S of the hard portion 92. The first direction D51 is inclined toward the proximal end side with respect to the direction orthogonal to the extending direction. An end surface on the proximal end side of the hard portion 92 is referred to as a "proximal end surface 92K." A virtual second direction D52 is defined that extends toward the outside along the proximal end surface 92K of the hard portion 92. The second direction D52 is inclined toward the distal end side with respect to the direction orthogonal to the extending direction. An acute angle, of angles formed between the first direction D51 and the extending direction, is defined as a first angle θ51. The first angle θ51 is an angle between 4 to 13 degrees, for example. The first angle θ51 is preferably 5 degrees. An acute angle, of angles formed between the second direction D52 and the extending direction is defined as a second angle θ52. The second angle θ52 is an angle between 5 to 16 degrees, for example. The second angle θ52 is preferably 16 degrees. The preferable five degrees of the first angle θ51 is smaller than the preferable sixteen degrees of the second angle θ52.

As shown in FIG. 18, a position of a boundary on the distal end side of the second portion 912 of the flexible portion 91, in other words, a position of a boundary between the second portion 912 and the third portion 913, is aligned, in the extending direction, with the position P11 of the end portion on the distal end side of the marker 22A. A position of a boundary on the proximal end side of the second portion 912 of the flexible portion 91, in other words, a position of a boundary between the first portion 911 and the second portion 912, is aligned, in the extending direction, with the position P21 of the end portion on the proximal end side of the marker 22B. Note that the hard portion 92 of the linear member 9 is laminated on the second portion 912 of the flexible portion 91. Thus, the inflatable region 33 of the balloon 3, the second portion 912 of the flexible portion 91, and the hard portion 92 are all disposed in the same position in the extending direction.

As shown in FIG. 19, two notches 51, which extend toward the inside in the radial direction from the outer portion 92B of the hard portion 92, are formed in the linear member 9. Each of the two notches 51 is formed by cutting out a part of the linear member 9. A cross-sectional shape of each of the notches 51 is a wedge shape. The two notches 51 are disposed side by side at an equal interval in the extending direction.

Each of the notches 51 includes surfaces 51A and 51B that face each other in the extending direction. When the balloon 3 is not in the inflated state, namely, in the state in which the force in the elongation direction is not acting on the linear member 9, a direction that extends to the outside along the surface 51A is inclined toward the proximal end side with respect to the direction orthogonal to the extending direction. A direction that extends to the outside along the surface 51B is inclined toward the distal end side with respect to the direction orthogonal to the extending direction. The surfaces 51A and 51B are disposed with an interval therebetween in the extending direction. A gap is formed between the surfaces 51A and 51B. The surfaces 51A and 51B are connected by respective inside end portions thereof. The end portions that connect the surfaces 51A and 51B are, in other words, an end portion (hereinafter referred to as a "bottom portion") 51C of the inside of the notch 51. The bottom portion 51C is positioned further to the inside, in the radial direction, than the boundary 912B that represents the boundary between the second portion 912 of the flexible portion 91 and the hard portion 92.

When the balloon 3 inflates as a result of the compressed fluid being supplied from the hub 5, the force in the elongation direction acts on the first portion 911 and the third portion 913 of the flexible portion 91 of the linear member 9. As a result, the first portion 911 and the third portion 913 elastically deform so as to extend along the extending direction. Further, of the linear member 9, the force in the extending direction also acts on the section at which the second portion 912 of the flexible portion 91 and the hard portion 92 are laminated. Here, in comparison to the flexible portion 91, the hard portion 92 does not easily extend. As a result of the second portion 912 of the flexible portion 91 elastically deforming due to the force in the extending direction, the respective surfaces 51A and 51B of the plurality of notches 51 separate from each other in the extending direction. As a result, the elastic deformation of the second portion 912 of the flexible portion 91 is not easily suppressed by the hard portion 92. Thus, of the linear member 9, even the section in which the second portion 912 of the flexible portion 91 and the hard portion 92 are laminated elastically deforms so as to extend in the extending direction in accordance with the inflation of the balloon 3. As a result of the above, the linear member 9 follows the inflation of the balloon 3 and extends in the extending direction across the whole length of the linear member 9 in the extending direction.

Meanwhile, when the balloon 3 deflates as a result of the compressed fluid being discharged from the balloon 3 in the inflated state, the flexible portion 91 of the linear member 9 that is extended in the extending direction contracts due to a restoring force. The surfaces 51A and 51B of the notches 51 of the hard portion 92 of the linear member 9 approach each other with a space therebetween in the extending direction. The linear member 9A is covered from the outside by the pleat 3A, the linear member 9B is covered from the outside by the pleat 3B, and the linear member 9C is covered from the outside by the pleat 3C.

Main Operations and Effects of Sixth Embodiment

In the balloon catheter 90, when the balloon 3 is inflated, the force that tries to elongate acts on the linear member 9. If the linear member 9 does not extend well even when this force is acting, the linear member 9 cannot follow the inflation of the balloon 3 and there is a possibility that the linear member 9 may break away from the balloon 3. Further, there is a case in which the inflation of the balloon 3 is obstructed by the linear member 9. Thus, it is preferable that the extendability of the linear member 9 be high. On the other hand, in order to cause the linear member 9 to act appropriately on the blood vessel when the balloon 3 is inflated, it is preferable that the hardness of the linear member 9 be harder.

In response to this, in the balloon catheter 90, when the balloon 3 is inflated, the outer portion 92B of the hard portion 92 of the linear member 9 protrudes to the outside with respect to the balloon 3. The hardness of the hard portion 92 is harder than the flexible portion 91. Thus, the linear member 9 can cause the hard portion 92 to act appropriately on the blood vessel when the balloon 3 is inflated. For example, since the outer portion 92B of the hard portion 92 is peaked, the hard portion 92 easily bites into the lesioned part (not shown in the drawings) of the blood vessel. As a result, in a state in which the linear member 9 causes the balloon 3 to be in a state of not easily slipping with respect to the lesioned part of the blood vessel, the lesioned part can be expanded from inside by the inflation of the balloon 3.

The flexible portion 91 of the linear member 9 can extend. Thus, when the linear member 9 tries to extend in accordance with the inflation of the balloon 3, the first portion 911 and the third portion 913, of the flexible portion 91, on which the hard portion 92 is not laminated extend in a favorable manner, and follow the balloon 3. Further, the two notches 51 are formed in the linear member 9. Thus, when the second portion 912 of the flexible portion 91 tries to extend in accordance with the inflation of the balloon 3, the surfaces 51A and 51B of each of the notches 51 separate from each other, thus suppressing the hard portion 92 from obstructing the extending of the second portion 912 of the flexible portion 91. As a result, the linear member 9 can extend appropriately across the whole length of the linear member 9 in accordance with the inflation of the balloon 3, and can follow the inflation of the balloon 3. Thus, the balloon catheter 90 can inhibit the linear member 9 from breaking away from the balloon 3 when the balloon 3 is inflated, or inhibit the linear member 9 from obstructing the inflation of the balloon 3.

The bottom portion 51C of each of the notches 51 is positioned further to the inside, in the radial direction, than the boundary 912B between the second portion 912 of the flexible portion 91 and the hard portion 92. In this case, the hard portion 92 is divided into three by the two notches 51. Thus, the linear member 9 can appropriately suppress the hard portion 92 from obstructing the extending of the second portion 912 of the flexible portion 91. As a result, the balloon catheter 90 can even more appropriately inhibit the linear member 9 from breaking away from the balloon 3 when the balloon 3 is inflated, or inhibit the linear member 9 from obstructing the inflation of the balloon 3.

The surfaces 51A and 51B of each of the two notches 51 are disposed so as to be separated from each other in the extending direction. In this case, the linear member 9 can easily bend in the direction orthogonal to the extending direction at the section in which the notches 51 are formed. As a result, when the balloon 3 bends in the direction orthogonal to the extending direction, the balloon catheter 90 can cause the linear member 9 to follow the balloon 3 and bend. Thus, the balloon catheter 90 can suppress the linear member 9 from breaking away from the balloon 3 when the balloon 3 bends.

The linear member 9 is bonded to the outer peripheral surface of the balloon 3 between the distal end position M1 and the proximal end position M2. As a result, the linear member 9 is held in a fixed position with respect to the balloon 3. Thus, the balloon catheter 90 can cause the linear member 9 to act on the blood vessel when the balloon 3 is inflated, while the linear member 9 is held in a correct position with respect to the balloon 3. Further, by directly bonding the linear member 9 to the balloon 3, the balloon catheter 90 can inhibit the position of the linear member 9 with respect to the balloon 3 from changing in accordance with the inflation of the balloon 3.

The first direction D51, which extends to the outside along the distal end surface 92S that is the end portion of the hard portion 92 on the distal end side, is inclined toward the proximal end side. In this case, when the balloon catheter 90 moves inside the blood vessel in the course of the user causing the balloon 3 to approach the constricted portion of the blood vessel, the linear member 9 can be inhibited from catching on the inner wall of the blood vessel. Thus, the user can smoothly move the balloon 3 as far as the constricted portion of the blood vessel. Further, the second direction D52, which extends to the outside along the proximal end surface 92K that is the end portion of the hard portion 92 on the proximal end side, is inclined toward the distal end side. In this case, when the balloon catheter 90 moves inside the blood vessel in the course of the user pulling the balloon catheter 90 out from the blood vessel, the linear member 9 can be inhibited from catching on the inner wall of the blood vessel. Thus, the user can easily pull the balloon catheter 90 out from the blood vessel.

The linear member 9 is formed of a synthetic resin. In this case, the linear member 9 that includes the flexible portion 91 and the hard portion 92 can be easily manufactured by injection molding, extrusion molding or the like.

Seventh Embodiment and Eighth Embodiment

A seventh embodiment and an eighth embodiment will be explained with reference to FIG. 20 and FIG. 21. In the seventh embodiment, in place of the notches 51 of the sixth embodiment, notches 52 (refer to FIG. 20) are formed in the linear member 9. In the eighth embodiment, in place of the notches 51 of the sixth embodiment, notches 53 (refer to FIG. 21) are formed in the linear member 9. Other parts of the configuration are the same as those of the sixth embodiment. Hereinafter, where the configuration is the same as that of the above-described embodiments, the same reference numerals are assigned and an explanation thereof is omitted.

Figure 20:
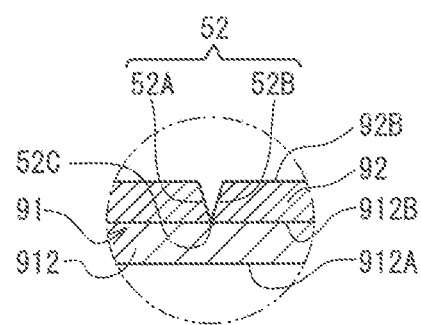
FIG. 20 is a cross-sectional view of an expanded part of the linear member according to a seventh embodiment.

As shown in FIG. 20, in the seventh embodiment, the notch 52 includes surfaces 52A and 52B. The end portion on the inside of the notch 52 is referred to as a "bottom portion 52C." The surfaces 52A and 52B, and the bottom portion 52C respectively correspond to the surfaces 51A and 51B, and the bottom portion 51C of the notch 51 of the sixth embodiment. In the notch 52, a position of the bottom portion 52C in the radial direction is different to that of the notch 51. In the notch 52, the bottom portion 52C is positioned in substantially the same position as the boundary 912B between the second portion 912 of the flexible portion 91 and the hard portion 92. In this case, similarly to the sixth embodiment, the hard portion 92 is divided into three in the extending direction by two of the notches 52. As a result, the linear member 9 can appropriately suppress the extending of the second portion 912 of the flexible portion 91 from being obstructed by the hard portion 92. Thus, similarly to the sixth embodiment, the balloon catheter 90 can even more appropriately inhibit the linear member 9 from breaking away from the balloon 3 when the balloon 3 is inflated, or inhibit the linear member 9 from obstructing the inflation of the balloon 3. In addition, in contrast to the sixth embodiment, a part of the notch 52 is not formed in the flexible portion 91. Therefore, in comparison to the case in which the part of the notch 51 is formed in the second portion 912 of the flexible portion 91 as in the sixth embodiment, the strength of the second portion 912 of the flexible portion 91 is maintained when extending.

Figure 21:
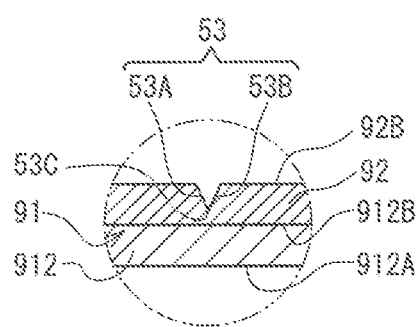
FIG. 21 is a cross-sectional view of an expanded part of the linear member according to an eighth embodiment.

As shown in FIG. 21, in the eighth embodiment, the notch 53 includes surfaces 53A and 53B. The end portion on the inside of the notch 53 is referred to as a "bottom portion 53C." The surfaces 53A and 53B, and the bottom portion 53C respectively correspond to the surfaces 51A and 51B, and the bottom portion 51C of the notch 51 of the above-described embodiment. In the notch 53, a position of the bottom portion 53C in the radial direction is different to that of the notches 51 and 52. In the notch 53, the bottom portion 53C is positioned further to the outside than the boundary 912B between the second portion 912 of the flexible portion 91 and the hard portion 92.

When the notch 53 is formed in the linear member 9, in contrast to the sixth embodiment and the seventh embodiment, the hard portion 92 is not divided in the extending direction by the notch 53. However, of the hard portion 92, a portion further to the inside than the bottom portion 53C of the notch 53 extends easily in the extending direction, compared to a portion in which the notch 53 is not formed. Therefore, of the linear member 9, the portion in which the second portion 912 of the flexible portion 91 and the hard portion 92 are laminated extends in the extending direction in accordance with the inflation of the balloon 3. Thus, similarly to the sixth embodiment and the seventh embodiment, the balloon catheter 90 can inhibit the linear member 9 from breaking away from the balloon 3 when the balloon 3 is inflated, or inhibit the linear member 9 from obstructing the inflation of the balloon 3.

The depth of the notch 53 is smaller than that of the notches 51 and 52, and therefore, the space between the surfaces 53A and 53B can be minimized when the surfaces 53A and 53B separate from each other in accordance with the inflation of the balloon 3. As a result, an area of the outer portion 92B of the hard portion 92 can be made larger than in the case of the sixth embodiment and the seventh embodiment. Note that, when the balloon 3 is inflated, the outer portion 92B of the hard portion 92 comes into contact with the blood vessel wall. Thus, since the balloon catheter 90 can increase the area of the portion (the outer portion 92B of the hard portion 92) of the linear member 9 that comes into contact with the blood vessel wall, the balloon catheter 90 can cause the linear member 9 to act appropriately on the blood vessel when the balloon 3 is inflated.

Ninth Embodiment

A ninth embodiment will be explained with reference to FIG. 22. In the ninth embodiment, incisions 54 are formed in place of the notches 51 of the sixth embodiment. Other parts of the configuration are the same as those of the sixth to eighth embodiments. Hereinafter, where the configuration is the same as that of the above-described embodiments, the same reference numerals are assigned and an explanation thereof is omitted.

Figure 22:
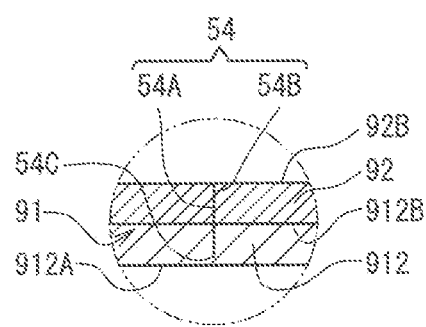
FIG. 22 is a cross-sectional view of an expanded part of the linear member according to a ninth embodiment.

As shown in FIG. 22, the incision 54 extends to the inside along the radial direction, from the outer portion 92B of the hard portion 92. The incision 54 includes surfaces 54A and 54B that face each other in the extending direction. An end portion (hereinafter referred to as a "bottom portion") 54C on the inside of each of the incisions 54 is positioned further to the inside, in the radial direction, than the boundary 912B between the second portion 912 of the flexible portion 91 and the hard portion 92.

When the compressed fluid is not supplied from the hub 5 and the balloon 3 is not in the inflated state, the force in the elongation direction does not act on the linear member 9. In this case, as shown in FIG. 22, the surfaces 54A and 54B are in contact with each other. A gap is not formed between the surfaces 54A and 54B. On the other hand, when the balloon 3 is inflated as a result of the compressed fluid being supplied from the hub 5, the force in the elongation direction acts on the portion, of the linear member 9, at which the second portion 912 of the flexible portion 91 and the hard portion 92 are laminated. The surfaces 54A and 54B of the incision 54 separate from each other in the extending direction, as a result of the elastic deformation of the second portion 912 of the flexible portion 91. The hard portion 92 is divided in the extending direction by the incisions 54. Thus, the elastic deformation of the second portion 912 of the flexible portion 91 is not easily suppressed by the hard portion 92. As a result, the portion of the linear member 9 at which the second portion 912 of the flexible portion 91 and the hard portion 92 are laminated extends in the extending direction in accordance with the inflation of the balloon 3. Meanwhile, when the balloon 3 is deflated as a result of the compressed fluid being discharged from the balloon 3 in the inflated state, the flexible portion 91 of the linear member 9 that is extended in the extending direction contracts due to the restoring force. The surfaces 54A and 54B of the incision 54 of the hard portion 92 once more come into contact with each other. The surfaces 54A and 54B return to the state in which the gap is not formed therebetween.

Main Operations and Effects of Ninth Embodiment

As described above, in the ninth embodiment, the surfaces 54A and 54B of the incision 54 are in contact with each other when the balloon 3 is not inflated and the gap between them is not formed. In this case, even when the surfaces 54A and 54B separate from each other as a result of the inflation of the balloon 3, the gap between the surfaces 54A and 54B can be suppressed to a minimum. Thus, the area of the outer portion 92B of the hard portion 92 of the linear member 9 can be made as large as possible. As a result, since the balloon catheter 90 can make the area of the portion (the outer portion 92B of the hard portion 92) of the linear member 9 that comes into contact with the blood vessel wall as large as possible, the balloon catheter 90 can cause the linear member 9 to act even more appropriately on the blood vessel when the balloon 3 is inflated.

It should be noted that, in the ninth embodiment, similarly to the case of the notch 52 (refer to FIG. 20) of the seventh embodiment, the bottom portion 54C may be positioned in substantially the same position as the boundary 912B between the second portion 912 of the flexible portion 91 and the hard portion 92. Further, in the ninth embodiment, similarly to the case of the notch 53 (refer to FIG. 21) of the eighth embodiment, the bottom portion 54C may be positioned further to the outside than the boundary 912B between the second portion 912 of the flexible portion 91 and the hard portion 92.

The notch 51 of the sixth embodiment, the notch 52 of the seventh embodiment, the notch 53 of the eighth embodiment, and the incision 54 of the ninth embodiment may also be formed in the linear members 4, 6, 7, and 8 of the balloon catheters 10, 20, 40, and 50 according to the first to fifth embodiments.

For example, a state of the linear member 4 will be explained when the balloon 3 inflates as a result of the compressed fluid being supplied from the hub 5, in a case in which a plurality of the notches 51 are formed in the linear member 4 of the balloon catheter 10 according to the first embodiment. In accordance with the inflation of the balloon 3, the hard portion 42 of the linear member 4 tries to move away from the protruding portion 225 of the inner tube 22. At this time, the force in the elongation direction acts on the first portion 411 and the third portion 413 of the flexible portion 41 of the linear member 4. As a result, the first portion 411 and the third portion 413 elastically deform so as to extend in the extending direction. Thus, the hard portion 42 separates easily from the protruding portion 225 of the inner tube 22. Further, the force in the extending direction also acts on the section of the linear member 4 at which the second portion 412 of the flexible portion 41 and the hard portion 42 are laminated. Here, the respective surfaces 51A and 51B of the plurality of notches 51 of the flexible portion 41 separate from each other in the extending direction in accordance with the elastic deformation of the second portion 412 of the flexible portion 41 caused by the force in the extending direction. As a result, the elastic deformation of the second portion 412 of the flexible portion 41 is not easily suppressed by the hard portion 42. Therefore, the section of the linear member 4 at which the second portion 412 of the flexible portion 41 and the hard portion 42 are laminated also elastically deforms so as to extend in the extending direction in accordance with the inflation of the balloon 3. As a result of the above, the linear member 4 extends in the extending direction over the whole length of the linear member 4 in the extending direction.

Meanwhile, when the balloon 3 deflates as a result of the compressed fluid being discharged from the balloon 3 in the inflated state, the flexible portion 41 of the linear member 4 that is extended in the extending direction contracts due to the restoring force. The surfaces 51A and 51B of the notches 51 of the hard portion 42 of the linear member 4 approach each other with the space therebetween in the extending direction. The hard portion 42 of the linear member 4 moves closer to the protruding portion 225 of the inner tube 22. The warping of the linear member 4 is suppressed by the linear member 4 contracting.

As described above, when the notches 51 are formed in the linear member 4 of the balloon catheter 10, the linear member 4 can be caused to appropriately extend over the whole length of the linear member 4 in accordance with the inflation of the balloon 3. As a result, the balloon catheter 10 can inhibit the linear member 4 from breaking away from the balloon 3 when the balloon 3 is inflated, or inhibit the linear member 4 from obstructing the inflation of the balloon 3. Further, in the case of the balloon catheter 10, the end portion on the distal end side of the linear member 4 is connected to the balloon 3, and the end portion on the proximal end side of the linear member 4 is connected to the catheter shaft 2 via the mounting member 21A. Other portions of the linear member 4 are not bonded to the balloon 3. Further, when the linear member 4 is bonded to the catheter shaft 2, a manufacturing process is easier than when the linear member 4 is bonded to the balloon 3. Thus, the manufacturing of the balloon catheter 10 can be simplified.

In the above description, a part of the portion of the linear member 4 excepting both the end portions on the distal end side and the proximal end side may be bonded to the balloon 3. For example, the second portion 412 of the flexible portion 41 of the linear member 4 may be bonded to the inflatable region 33 of the balloon 3.

Modified Examples

The present disclosure is not limited to the above-described embodiments and various modifications are possible. The number of the linear members 4, 6, 7, 8, and 9 is not limited to three, and may be another quantity. The linear members 4, 6, 7, 8, and 9 are members that extend in a substantially straight line along the extending direction. In contrast, the linear members 4, 6, 7, 8, and 9 may be members that extend in a spiral shape along the extending direction. The hard portions 42 and 92 may be provided across the whole length of the flexible portions 41 and 91 in the extending direction.

The outer portions of the hard portions 42, 62 (the first portion 621), 71 (the second portion 712), 82, and 92, which are each disposed in a position corresponding to the inflatable region 33 of the balloon 3, correspond to the equilateral triangle shape and are peaked. The outer portions of the hard portions 42, 62, 71, 82, and 92 have the function of suppressing the slipping of the balloon 3. The shape of the outer portions of the hard portions 42, 62, 71, 82, and 92 is not limited to that of the above-described embodiments. For example, an angle of the outer portions of the hard portions 42, 62, 71, 82, and 92 may be steep. In this case, the outer portions of the hard portions 42, 62, 71, 82, and 92 may function, for example, as a cutting blade for cutting open the lesioned part when the balloon 3 is in the inflated state.

The cross-sectional shape of the linear members 4, 6, 7, 8, and 9 is not limited to the above-described examples. For example, the cross-sectional shape of the hard portions 42, 62, 71, 82, and 92 may be an isosceles triangle shape or a triangle shape having three sides of mutually differing lengths. In the first embodiment, the cross-sectional shape of the flexible portion 41 may be a semi-circle that is cut out from the outside, or may be a polygonal shape. The cross-sectional shape including the flexible portion 41 and the hard portion 42 may be a circular shape, or may be a polygonal shape. Note that this also applies to the second to ninth embodiments.

In the above-described embodiments, the end portions on the distal end side of the linear members 4, 6, 7, 8, and 9 are connected to the distal end side leg portion 35, at the distal end position M1. In contrast to this, the end portions on the distal end side of the linear members 4, 6, 7, 8, and 9 may be connected to the inner tube 22. The end portion on the proximal end side of the linear member 4 is connected to the mounting member 21A. The end portions on the proximal end side of the linear members 6, 7, 8, and 9 are connected to the proximal end side leg portion 31. In contrast to this, the end portions on the proximal end side of the linear members 4, 6, 7, 8, and 9 may be connected to the outer tube 21.

The end portion on the proximal end side of the linear member 4 need not necessarily be able to move along the extending direction. Specifically, for example, the end portion on the proximal end side of the linear member 4 may be connected to the outer peripheral surface of the outer tube 21, further toward the proximal end side than the portion, of the outer tube 21, at which the proximal end side leg portion 31 of the balloon 3 is connected.

Each of the first directions D11, D21, D31, D41, and D51 is inclined toward the proximal end side with respect to the direction orthogonal to the extending direction. Each of the second directions D12, D22, D32, D42, and D52 is inclined toward the distal end side with respect to the direction orthogonal to the extending direction. In contrast to this, the first directions D11, D21, D31, D41, and D51 and the second directions D12, D22, D32, D42, and D52 may extend in the direction orthogonal to the extending direction. The preferable five degrees of each of the first angles θ11, θ21, θ31, θ41, and θ51 is smaller than the preferable sixteen degrees of each of the second angles θ12, θ22, θ32, θ42, and θ52. In contrast to this, a preferable value of each of the first angles θ11, θ21, θ31, θ41, and θ51 may be the same as a preferable value of each of the second angles θ12, θ22, θ32, θ42, and θ52. Further, the preferable value of each of the first angles θ11, θ21, θ31, θ41, and θ51 may be larger than the preferable value of each of the second angles θ12, θ22, θ32, θ42, and θ52.

The proximal end side thicknesses R11, R21, R31, and R41 are larger than the distal end side thicknesses R13, R23, R33, and R43. In contrast to this, the proximal end side thicknesses R11, R21, R31, and R41 may be the same as the distal end side thicknesses R13, R23, R33, and R43. The proximal end side thicknesses R11, R21, R31, and R41 may be smaller than the distal end side thicknesses R13, R23, R33, and R43. The proximal end side thickness R51 may be larger or smaller than the distal end side thickness R53.

The position of the boundary on the distal end side of the inflatable region 33 is aligned, in the extending direction, with the position P11 of the end portion on the distal end side of the marker 22A. The position of the boundary on the proximal end side of the inflatable region 33 is aligned, in the extending direction, with the position P21 of the end portion on the proximal end side of the marker 22B. However, the position of the boundary on the distal end side of the inflatable region 33 need not necessarily be completely aligned, in the extending direction, with the position P11 on the distal end side of the marker 22A. For example, the position of the boundary on the distal end side of the inflatable region 33 may be aligned, in the extending direction, with any position between the position P11 of the end portion on the distal end side of the marker 22A and a position P12 of the end portion on the proximal end side of the marker 22A. The position of the boundary on the proximal end side of the inflatable region 33 need not necessarily be completely aligned, in the extending direction, with the position P21 on the proximal end side of the marker 22B. For example, the position of the boundary on the proximal end side of the inflatable region 33 may be aligned, in the extending direction, with any position between the position P21 of the end portion on the proximal end side of the marker 22B and a position P22 of the end portion on the distal end side of the marker 22B. In other words, it is sufficient that the positions of the marker 22A and the marker 22B respectively correspond to the position of the boundary on the distal end side of the inflatable region 33 and the position of the boundary on the proximal end side of the inflatable region 33. Further, the number of the markers is not limited to two, and may be three or more.

Each of the boundary portion between the proximal end side cone region 32 and the inflatable region 33 and the boundary portion between the inflatable region 33 and the distal end side cone region 34 of the balloon 3 in the inflated state may be curved. In this case, for example, with respect to the positions of each of the boundaries, when a plurality of virtual planes that touch the respectively curved boundary portions are defined, positions of the boundary portions that touch the virtual plane, of the plurality of virtual planes, that forms an acute angle of 45 degrees with the extending direction may be the positions of each of the boundaries. Further, in the above-described embodiments, each of the proximal end side cone region 32 and the distal end side cone region 34 is a region whose diameter changes linearly from the proximal end side toward the distal end side. However, each of the proximal end side cone region 32 and the distal end side cone region 34 may be a region whose diameter changes in a curved manner from the proximal end side toward the distal end side. In addition, one of the proximal end side cone region 32 and the distal end side cone region 34 may be the region whose diameter changes in the curved manner and the other may be the region whose diameter changes linearly.

The distal end surfaces 42S, 62S, 72S, 82S, and 92S, and the proximal end surfaces 42K, 62K, 72K, 82K, and 92K of the linear members 4, 6, 7, 8, and 9 need not necessarily have a straight line shape. For example, at least either of the distal end surfaces 42S, 62S, 72S, 82S, and 92S, or the proximal end surfaces 42K, 62K, 72K, 82K, and 92K may have level differences.

The outer portions 412B and 912B have a straight line shape. The outer portions 412B and 912B may have a curved shape. In other words, for example, the hard portions 42 and 92 may have a circular arc-shaped cross section.

The present disclosure can be applied to a device other than the balloon catheter that includes the balloon 3 that is inflated by the supply of the compressed fluid. For example, the linear members 4, 6, 7, 8, and 9 may be applied to a device that has a mechanically expanding mechanism in place of the balloon 3. In the above-described embodiments, the example is given of the catheter shaft 2 that has the outer tube 21 and the inner tube 22. In the present disclosure, the catheter shaft 2 need not necessarily have the outer tube 21 and the inner tube 22. For example, the catheter shaft 2 may have only one flexible tube.

In the sixth to ninth embodiments, the positions in the radial direction of the bottom portions 51C to 53C of each of the notches 51 to 53, and the bottom portions 54C of the incisions 54 may be positions that are substantially the same position as the inner portion 912A of the second portion 912 of the flexible portion 91. In other words, the linear member 9 may be divided in the extending direction by the notches 51 to 53 or the incisions 54.

In the sixth to eighth embodiments, the cross-sectional shape of the notches 51 to 53 is not limited to the wedge shape. For example, a notch may be a slit whose cross-sectional shape is a semi-circular shape, a rectangular shape, a trapezoid shape or the like, or may be a slit whose outside end portions are rounded. Further, a plurality of slits having mutually different cross-sectional shapes may be formed in the linear member 9. When the notch has the semi-circular shape, the rectangular shape, the trapezoid shape or the like, the position of a bottom portion thereof may be further to the inside or to the outside, in the radial direction, than the boundary 912B between the second portion 912 of the flexible portion 91 and the hard portion 92. In addition, the position of the bottom portion may be a position that is substantially the same position as the boundary 912B in the radial direction. The number of the notches 51 to 53 formed in the linear member 9 is not limited to two, and may be another quantity, such as one or more, for example.

In the ninth embodiment, the incision 54 may extend in a direction intersecting with the radial direction, to the inside from the outer portion 92B of the hard portion 92. The shape of the incision 54 is not limited to the straight line and may be a curved line. The incision may be a slit whose outside end portions are rounded. Further, a plurality of slits including the notches and the incisions having mutually different shapes may be formed in the linear member 9.

In the sixth to ninth embodiments, the linear member 9 may be bonded to the balloon 3 only in the vicinity of each of the distal end position M1 and the proximal end position M2. Of the linear member 9, a section excluding the vicinity of each of the distal end position M1 and the proximal end position M2 need not necessarily be bonded to the balloon 3. The end portion on the distal end side of the linear member 9 may be connected to the inner tube 22. The end portion on the proximal end side of the linear member 9 may be connected to the outer tube 21.

In the sixth to ninth embodiments, the flexible portion 91 of the linear member 9 includes the first portion 911, the second portion 912, and the third portion 913. However, the flexible portion 91 need not necessarily include the first portion 911 and the third portion 913. For example, the linear member 9 may be configured by the hard portion 92 and the second portion 912. In this case, the second portion 912 is bonded with the outer peripheral surface of the inflatable region 33 of the balloon 3 using adhesive or the like. In addition, the flexible portion 91 of the linear member 9 may be configured by the second portion 912 and one of the first portion 911 and the third portion 913.

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. A balloon catheter comprising:
a balloon/shaft assembly that includes a catheter shaft extending from a proximal end to a distal end and a balloon connected to the catheter shaft, the balloon having an inflatable region configured to inflate outward in a radial direction around the catheter shaft; and
a linear member straddling the inflatable region of the balloon and being mounted on the balloon/shaft assembly at a distal end position located further toward a distal end side than the inflatable region and at a proximal end position located further toward a proximal end side than the inflatable region, and
wherein the linear member includes:
a hard portion that includes at least an outer portion disposed on an opposite side to an inner portion facing the inflatable region, of a portion disposed along an outer peripheral surface of the inflatable region in an inflated state, and
a flexible portion that is a portion other than the hard portion, the flexible portion being extendable and having a lower hardness than the hard portion,
wherein the flexible portion extends between the distal end position and the proximal end position,
wherein the hard portion protrudes to the outside from the outer portion of a portion of the flexible portion that is disposed along the outer peripheral surface of the inflatable region in the inflated state,
wherein a slit is formed extending toward the inside in the radial direction from an end portion on the outside of the hard portion,
wherein a bottom portion is positioned, in the radial direction, substantially in the same position as a boundary between the flexible portion and the hard portion, the bottom portion being a portion furthermost to the inside of the slit, and
wherein, a thickness of a portion of the flexible portion located further toward the distal end side than the hard portion is narrower than a thickness of a portion of the flexible portion located further toward the proximal end side than the hard portion.

2. The balloon catheter according to claim 1, wherein a direction extending to the outside along a distal end portion is inclined toward a proximal end side, the distal end portion being an end portion on the distal end side of the hard portion.

3. The balloon catheter according to claim 1, wherein a direction extending to the outside along a proximal end portion is inclined toward the distal end side, the proximal end portion being an end portion on the proximal end side of the hard portion.

4. The balloon catheter according to claim 1, wherein
a first direction extending to the outside along a distal end portion is inclined toward the proximal end side, the distal end portion being an end portion on the distal end side of the hard portion,
a second direction extending to the outside along a proximal end portion is inclined toward the distal end side, the proximal end portion being an end portion on the proximal end side of the hard portion, and
an angle of the first direction with respect to an extending direction of the catheter shaft is smaller than an angle of the second direction with respect to the extending direction of the catheter shaft.

5. The balloon catheter according to claim 1, wherein the slit is a notch where a part of the linear member is cut out.

6. The balloon catheter according to claim 1, wherein the slit is an incision having two surfaces that face each other and are in contact with each other.

7. The balloon catheter according to claim 1, wherein at least a part of the flexible portion of the linear member is bonded to the balloon.

8. The balloon catheter according to claim 1, wherein the linear member is disposed along an outer peripheral surface of the balloon in the inflated state.

9. The balloon catheter according to claim 1, wherein
two radiopaque markers are respectively provided in two positions separated from each other in an extending direction of the catheter shaft,
of the two radiopaque markers, a position of a marker provided on the distal end side corresponds to a position of a boundary of the inflatable region on the distal end side, in the extending direction of the catheter shaft, and
of the two radiopaque markers, a position of a marker provided on the proximal end side corresponds to a position of a boundary of the inflatable region on the proximal end side, in the extending direction of the catheter shaft.

10. The balloon catheter according to claim 1, wherein
the balloon includes a proximal end side leg portion bonded to the catheter shaft at a position further toward the distal end side than the proximal end position, and
an end portion on the proximal end side of the linear member is bonded to the balloon/shaft assembly at the proximal end position.

11. The balloon catheter according to claim 1, wherein
the balloon includes a proximal end side leg portion bonded to the catheter shaft at the proximal end position, and
an end portion on the proximal end side of the linear member is bonded to an outer peripheral surface of the proximal end side leg portion.

12. The balloon catheter according to claim 1, wherein the linear member is formed of a synthetic resin.

13. The balloon catheter according to claim 1, wherein the linear member includes end portions in an extending direction, at least one of the end portions being connected to the catheter shaft.

14. The balloon catheter according to claim 1, wherein the thickness of the portion of the flexible portion located further toward the distal end side than the hard portion is constant.

15. A balloon catheter comprising:
a balloon/shaft assembly that includes a catheter shaft extending from a proximal end to a distal end and a balloon connected to the catheter shaft, the balloon having an inflatable region configured to inflate outward in a radial direction around the catheter shaft; and
a linear member straddling the inflatable region of the balloon and being mounted on the balloon/shaft assembly at a distal end position located further toward a distal end side than the inflatable region and at a proximal end position located further toward a proximal end side than the inflatable region, and wherein the linear member includes:
a hard portion that includes at least an outer portion disposed on an opposite side to an inner portion facing the inflatable region, of a portion disposed along an outer peripheral surface of the inflatable region in an inflated state, and
a flexible portion that is a portion other than the hard portion, the flexible portion being extendable and having a lower hardness than the hard portion,
wherein the flexible portion extends between the distal end position and the proximal end position,
wherein the hard portion protrudes to the outside from the outer portion of a portion of the flexible portion that is disposed along the outer peripheral surface of the inflatable region in the inflated state,
wherein a slit is formed extending toward the inside in the radial direction from an end portion on the outside of the hard portion,
wherein a bottom portion is positioned further to the outside, in the radial direction, than a boundary between the flexible portion and the hard portion, the bottom portion being a portion furthermost to the inside of the slit, and
wherein, a thickness of a portion of the flexible portion located further toward the distal end side than the hard portion is narrower than a thickness of a portion of the flexible portion located further toward the proximal end side than the hard portion.

16. The balloon catheter according to claim 15, wherein a direction extending to the outside along a distal end portion is inclined toward a proximal end side, the distal end portion being an end portion on the distal end side of the hard portion.

17. The balloon catheter according to claim 15, wherein a direction extending to the outside along a proximal end portion is inclined toward the distal end side, the proximal end portion being an end portion on the proximal end side of the hard portion.

18. The balloon catheter according to claim 15, wherein
a first direction extending to the outside along a distal end portion is inclined toward the proximal end side, the distal end portion being an end portion on the distal end side of the hard portion,
a second direction extending to the outside along a proximal end portion is inclined toward the distal end side, the proximal end portion being an end portion on the proximal end side of the hard portion, and
an angle of the first direction with respect to an extending direction of the catheter shaft is smaller than an angle of the second direction with respect to the extending direction of the catheter shaft.

19. The balloon catheter according to claim 15, wherein the slit is a notch where a part of the linear member is cut out.

20. The balloon catheter according to claim 15, wherein the slit is an incision having two surfaces that face each other and are in contact with each other.

21. The balloon catheter according to claim 15, wherein at least a part of the flexible portion of the linear member is bonded to the balloon.

22. The balloon catheter according to claim 15, wherein the linear member is disposed along an outer peripheral surface of the balloon in the inflated state.

23. The balloon catheter according to claim 15, wherein
two radiopaque markers are respectively provided in two positions separated from each other in an extending direction of the catheter shaft,
of the two radiopaque markers, a position of a marker provided on the distal end side corresponds to a position of a boundary of the inflatable region on the distal end side, in the extending direction of the catheter shaft, and
of the two radiopaque markers, a position of a marker provided on the proximal end side corresponds to a position of a boundary of the inflatable region on the proximal end side, in the extending direction of the catheter shaft.

24. The balloon catheter according to claim 15, wherein
the balloon includes a proximal end side leg portion bonded to the catheter shaft at a position further toward the distal end side than the proximal end position, and
an end portion on the proximal end side of the linear member is bonded to the balloon/shaft assembly at the proximal end position.

25. The balloon catheter according to claim 15, wherein
the balloon includes a proximal end side leg portion bonded to the catheter shaft at the proximal end position, and
an end portion on the proximal end side of the linear member is bonded to an outer peripheral surface of the proximal end side leg portion.

26. The balloon catheter according to claim 15, wherein the linear member is formed of a synthetic resin.

27. The balloon catheter according to claim 15, wherein the linear member includes end portions in an extending direction, at least one of the end portions being connected to the catheter shaft.

28. The balloon catheter according to claim 15, wherein the thickness of the portion of the flexible portion located further toward the distal end side than the hard portion is constant.

* * * * *